United States Patent
Tajima

(10) Patent No.: US 9,857,308 B2
(45) Date of Patent: Jan. 2, 2018

(54) CHEMILUMINESCENCE MEASUREMENT DEVICE AND METHOD FOR SAME

(71) Applicant: Universal Bio Research Co., Ltd., Matsudo-shi, Chiba (JP)

(72) Inventor: Hideji Tajima, Matsudo (JP)

(73) Assignee: UNIVERSAL BIO RESEARCH CO., LTD., Matsudo-Shi, Chiba (JP)

( * ) Notice: Subject to any disclaimer, the term of this patent is extended or adjusted under 35 U.S.C. 154(b) by 0 days.

(21) Appl. No.: 15/027,297

(22) PCT Filed: Oct. 7, 2014

(86) PCT No.: PCT/JP2014/076860
§ 371 (c)(1),
(2) Date: Apr. 5, 2016

(87) PCT Pub. No.: WO2015/053290
PCT Pub. Date: Apr. 16, 2015

(65) Prior Publication Data
US 2016/0245756 A1 Aug. 25, 2016

(30) Foreign Application Priority Data
Oct. 7, 2013 (JP) .................................. 2013-210598

(51) Int. Cl.
*G01N 21/76* (2006.01)
*G01N 35/00* (2006.01)
*G01N 35/10* (2006.01)

(52) U.S. Cl.
CPC ......... *G01N 21/76* (2013.01); *G01N 35/0098* (2013.01); *G01N 35/1002* (2013.01); *Y10T 436/119163* (2015.01)

(58) Field of Classification Search
CPC .... G01N 21/76; G01N 35/0098; G01N 35/10; G01N 35/1002; Y10T 436/0098;
(Continued)

(56) References Cited

U.S. PATENT DOCUMENTS

| 4,472,352 A | 9/1984 | Quesneau |
| 5,290,513 A * | 3/1994 | Berthold ................ G01N 21/76 250/328 |

(Continued)

FOREIGN PATENT DOCUMENTS

| JP | 4-16205 | 4/1992 |
| JP | 2003302343 | 10/2003 |

(Continued)

OTHER PUBLICATIONS

Matsunaga et al. Analytica Chimica Acta, vol. 475, 2003, pp. 75-83.*

(Continued)

*Primary Examiner* — Maureen Wallenhorst
(74) *Attorney, Agent, or Firm* — Haynes and Boone, LLP

(57) ABSTRACT

The present invention relates to a device and method for measuring chemiluminescence, and an object is to provide a compact and reliable device and method for measuring chemiluminescence. The device includes a vessel group, a nozzle head having a gas suctioning and discharging mechanism, one or more nozzles, which are in communication with the suctioning and discharging mechanism, and to a front end of which a dispensing tip is attachable, and a magnetic force means capable of causing a magnetic field inside the attached dispensing tip, a nozzle moving mechanism, a linkage part provided to the nozzle head, linkable to the reaction vessel and capable of forming a confined space shielded from external light, a linkage part moving mechanism capable of moving the linkage part, a photometer, a shutter, and a reagent injection flow channel capable of injecting a reagent for chemiluminescence.

19 Claims, 12 Drawing Sheets

(58) Field of Classification Search
CPC ............. Y10T 436/10; Y10T 436/1002; Y10T 436/11; Y10T 436/119163; Y10T 436/2575
USPC ........... 436/43, 54, 149, 150, 164, 172, 180; 422/63, 68.1, 82.05, 82.08, 501, 509; 435/288.7
See application file for complete search history.

(56) References Cited

U.S. PATENT DOCUMENTS

| | | | | |
|---|---|---|---|---|
| 5,447,687 | A | * | 9/1995 | Lewis .................... G01N 21/76 250/361 C |
| 6,123,903 | A | | 9/2000 | Tajima |
| 7,879,290 | B2 | * | 2/2011 | Noda ....................... C12Q 1/04 422/52 |
| 2011/0262919 | A1 | * | 10/2011 | Tajima ................. C12Q 1/6804 435/6.11 |

FOREIGN PATENT DOCUMENTS

| | | |
|---|---|---|
| JP | 2011247859 | 12/2011 |
| WO | WO2008004695 | 1/2008 |

OTHER PUBLICATIONS

International Search Report and Written Opinion (and English translation) issued by the Japanese Patent Office regarding International Application No. PCT/JP2014/076860, dated Nov. 4, 2014, 13 pages.

International Preliminary Report on Patentability issued by the Japanese Patent Office regarding International Application No. PCT/JP2014/076860, dated Jan. 29, 2016, 16 pages.

* cited by examiner

CHEMILUMINESCENCE MEASUREMENT DEVICE AND METHOD FOR SAME

CROSS REFERENCE

This application is a United States national phase application of co-pending international patent application number PCT/JP2014/076860, filed Oct. 7, 2014, which claims priority to Japanese patent application number 2013-210598, filed Oct. 7, 2013, the entire disclosures of which are hereby incorporated herein by reference.

TECHNICAL FIELD

The present invention relates to a device and method for measuring chemiluminescence, which are suitable for immunological examinations or various medical examinations based on a chemiluminescence method, biochemical reactions including an amplification of DNA, and the like. In particular, the present invention relates to a device and method for measuring chemiluminescence, which are suitable for measuring analyses using a CLIA assay based on the principle that injection of a trigger reagent immediately produces luminescence when the treatment is carried out in a plurality of reaction vessels in parallel, or a CLEIA assay including labeling with an enzyme and measurement of the enzyme activity with the use of a chemiluminescence method.

BACKGROUND ART

In recent years, it is known that an examination based on a chemiluminescence method has very high sensitivity and has high reliability for the measurement, so that such an examination is not limited to an immunological examination but used in a wide field. For example, in order to measure an amount of amplified nucleic acids, a method for detecting an amplified product (RNAs) by measuring the strength of chemiluminescence with the use of an acridinium ester-labeled single strand DNA probe complementary to the amplified RNA strands is known. This method is used for detection of amplified RNAs (HPA measurement principle), which includes hybridizing a probe with a sample after completion of the amplification to form a double strand RNA-DNA hybrid, then deactivating acridinium ester of the unreacted probe that has not formed the hybrid through hydrolysis, in which acridinium ester of the probe that has formed the hybrid is protected and thus does not undergo the hydrolysis so that the chemiluminescence property is maintained, and measuring the strength of this chemiluminescence.

Accordingly, it is required to provide a more efficient and reliable autoanalyzer which is suitable also in the field in which a nucleic acid is handled.

However, there is a problem in that such a conventional autoanalyzer may require a complicated structure and control for carrying out light shielding because, when the autoanalyzer carries out measurement by guiding light between the above-mentioned reaction vessel and a PMT (photomultiplier tube), it is necessary to open and close a shutter provided to the PMT for protecting the PMT against noise light by driving its own motor for driving the shutter before bringing the reaction vessel into a light shielding state, and it is also necessary to guide the light along with the PMT while strictly maintaining the light shielding of the reaction vessel.

In order to carry out measurement, liquids targeted for measurement are transferred and dispensed into the reaction vessels for exclusive use in photometry provided in the vicinity of the PMT, or the vessels themselves are transferred to the location for measurement in the vicinity of the PMT one by one. Accordingly, in order to carry out measurement, the time is required to transfer the liquid or reaction vessel for every measurement. Therefore, when there are a large number of the reaction vessels to be measured, there is a problem in that the treatment time may increase.

In particular, when measurement of chemiluminescence is carried out by a CLIA assay, there is a problem in that a reliable measurement may not be carried out. This is because it is necessary to dispense a trigger reagent into the reaction vessels provided at the location for measurement in the vicinity of the PMT, by which the dispensed liquid is scattered to the PMT provided in the vicinity of the reaction vessels and the shutter for protecting the PMT against noise light, with the result that the PMT is contaminated and light reception is inhibited.

CITATION LIST

Patent Literature

Patent Literature 1: JP 3822637 B2

SUMMARY OF INVENTION

Technical Problem

Therefore, the present invention has been made in view of such existing circumstances, and it is a first object to provide a device and method for measuring chemiluminescence capable of simply and inexpensively achieving measurement of chemiluminescence with a simple device structure and control, without increasing the device size. It is a second object to provide a device and method for measuring chemiluminescence capable of quickly and effectively carrying out measurement of chemiluminescence. It is a third object to provide a reliable device and method for measuring chemiluminescence capable of carrying out measurement with a high degree of accuracy in a strictly light shielded atmosphere. It is a fourth object to provide a device and method for measuring chemiluminescence excellent in handleability capable of easily carrying out measurement with a simple operation.

Solution to Problem

The first invention is a device for measuring chemiluminescence, including a vessel group at least having one or more liquid reception parts and one or more reaction vessels, a nozzle head having a suctioning and discharging mechanism for carrying out suctioning and discharging of gas, one or more nozzles, which are in communication with the suctioning and discharging mechanism, and to a front end of which a dispensing tip is attachable, and a magnetic force means capable of causing a magnetic field inside the attached dispensing tip, a nozzle moving mechanism capable of moving the nozzle relative to the vessel group, a linkage part provided to the nozzle head, linkable to the reaction vessel through an opening thereof and capable of forming a confined space shielded from external light by means of linkage with the reaction vessel, a linkage part moving mechanism capable of moving the linkage part relative to the reaction vessel, a photometer, a shutter for bringing into a light guiding state between inside the reaction vessel and the photometer in relation to the linkage of the linkage part to the reaction vessel and bringing into a light shielding state between inside the reaction vessel and the photometer in relation to release of the linkage of the linkage part to the reaction vessel, and a reagent injection flow channel capable of injecting a reagent for chemiluminescence, which is provided to the linkage part, and a front end of which is located in the reaction vessel by means of the linkage of the linkage part to the reaction vessel.

Here, it is preferable that the "linkage part" be formed, for example, of a stopper-shaped or cover-shaped light shielding member. It is preferable that the linkage part be releasably linked to the reaction vessel through the opening thereby forming a confined space shielded from external light. The "linkage to the reaction vessel" is made by, for example, fitting to, covering of, and tight contacting to the opening of the reaction vessel. It is preferable that the "vessel group" additionally have one or more tip reception parts for receiving a dispensing tip attachable to the nozzle by means of the descent of the nozzle or the like, and that the liquid reception part have a sample reception part capable of receiving a sample, a liquid reception part capable of receiving a magnetic particle suspension capable of binding to a substance of interest, a liquid reception part capable of receiving a binding promoter, a liquid reception part capable of receiving a washing solution, a dissociating solution reception part capable of receiving a dissociating solution, and the like. "The reaction vessel" is required to, in case of being formed of a translucent material, have translucency for one portion corresponding to the portion (for example, a part of the sidewall or the bottom wall) of the reaction vessel through which light should pass, and have the other portion received in the reception part having a light shielding property such that the outer wall of the reaction vessel is covered, or in case of being formed of a material having a light shielding property, have a portion (for example, a part of the sidewall or the bottom wall) of the reaction vessel through which light should pass formed of a translucent member. For example, the "reception part" is a temperature control block having a light shielding property, to the sidewall or the bottom wall of which an optical element such as a rod lens which reaches the sidewall or the bottom wall of the reaction vessel is provided. In addition, it is preferable that the "reaction vessel" be temperature controllable by a temperature control part.

The "in relation to the linkage (or release thereof) of the linkage part to the reaction vessel" means that the linkage (or release thereof) is on the basis that the motion of linkage (or release thereof) has been carried out (mechanistically or electrically), or on the basis that the associated motion independent from the motion of linkage (or release thereof) has been carried out (mechanistically or electrically).

An example of the former is a case based on "interlocking of the linkage part with the shutter", and it is preferable in a point of convenience of control that the linkage part (including a member provided in the linkage part) be mechanistically (or mechanically) interlocked with the shutter so that the linkage part drives the opening/closing of the shutter. The "mechanistically (or mechanically) interlocked with" does not include a case of driving the opening/closing of the shutter by a motor based on a detective signal caused when the motion of the linkage part is detected by a sensor (electrically interlocked), but is included in the example of the former.

An example of the latter is based on, for example, injection (as associated motion carried out in linkage) of the reagent for chemiluminescence after the linkage of the linkage part to the reaction vessel, which brings into a light guiding state between inside the reaction vessel and the photometer, and on the basis that, for example, a predetermined measuring time mentioned below corresponding to the lifetime of the chemiluminescence has passed from injection of the reagent for chemiluminescence (as associated motion carried out after linkage and before release of the linkage), which brings into a light shielding state between inside the reaction vessel and the photometer.

The "photometer" contains a photoelectric element such as a photomultiplier tube (PMT) or a light receiving element.

Examples of chemiluminescent reaction used for measurement include 1) a luminol or isoluminol derivative/hydrogen peroxide, 2) an acridinium ester derivative/hydrogen peroxide, 3) an acridinium acylsulfonamide derivative, or the like. There are a CLIA method for chemiluminescence detection, in which a trigger reagent as the reagent for chemiluminescence is used (in case of an acridinium derivative, hydrogen peroxide is used in alkaline, or in case of an isoluminol derivative, hydrogen peroxide and micro-peroxidase (m-POD) are used) for direct labeling, and a CLEIA method for chemiluminescence detection for measurement of the labeled enzyme activity after labeling an enzyme. Because an enzyme is used for labeling, a method with no deactivation of the enzyme activity during B/F separation is required. For example, when peroxidase is used for detection, chemiluminescence is produced by a luminol/hydrogen peroxide system as a substrate. In case of measurement of glucose-6-phosphate dehydrogenase (G6PDH), when glucose-6-phosphate is used as a substrate, and NADP is used as a coenzyme, NADPH is generated through enzymatic reaction, so that detection may be made by chemiluminescent reaction of the NADPH.

Note that a confined space formed by the linkage part and the reaction vessel, and a portion optically connectable to the confined space, that is, the shutter, a portion in which light guiding is carried out between the reaction vessel and the photometer, and the PMT of the photometer are shielded from external light, except a portion through which light should pass. In doing so, for example, these are received as a whole in a dark room or a dark box, or the respective linkage part, reaction vessel, portion in which light guiding is carried out and PMT of the photometer, except a portion through which light should pass, are coated with a light shielding membrane, formed of an opaque material excellent in the light shielding property, provided with various colors excellent in the light shielding property, or done in combination thereof. In addition, it is preferable that these connection portions be provided with a packing having a light shielding property.

Switching of the shutter is carried out with the use of, for example, the movement in the vertical direction for linking the linkage part to the reaction vessel or releasing the linkage by the linkage part moving mechanism. In this case, switching between a light guiding state and a light shielding state may be achieved by providing a member in which a translucent portion and a non-translucent portion disposed in the vertical direction have an interval of the same distance as a moving distance of the linkage part.

Here, a confined space formed by the linkage part and the reaction vessel, and a portion optically connectable to the confined space, that is, the reagent injection flow channel, the shutter, a portion in which light guiding is carried out between the reaction vessel and the photometer, and the PMT of the photometer are shielded from external light, except a portion through which light should pass. In doing so, for example, these are received as a whole in a dark room or a dark box, or the respective linkage part, reaction vessel, portion in which light guiding is carried out and PMT of the photometer, except a portion through which light should pass, are coated with a light shielding membrane, formed of an opaque material excellent in the light shielding property, provided with various colors excellent in the light shielding property, or done in combination thereof. In addition, it is preferable that these connection portions be provided with a packing having a light shielding property.

The "reagent for chemiluminescence" is a trigger reagent in case of a CLIA method. The "trigger reagent" is a reagent which is injected to produce chemiluminescence in various chemiluminescent reactions. For example, when used in the above mentioned chemiluminescence reactions, in case of an acridinium derivative as the trigger reagent, hydrogen peroxide is used in alkaline, and in case of an isoluminol derivative thereas, hydrogen peroxide and micro-peroxidase (m-POD) are used. In addition, in a CLEIA method, it is a substrate.

The second invention is a device for measuring chemiluminescence, further including one or more light guiding part capable of guiding light between the reaction vessel and the photometer, in which the shutter switches the light guiding part between a light guiding state and a light shielding state.

Here, the "light guiding part" contains, in addition to an optical fiber, an optical element such as a lens or a rod lens. Note that the shutter switches the light guiding part between a light guiding state and a light shielding state interlocking with the linkage part usually when the linkage part is moved in the vertical direction by the linkage part moving mechanism to link to the reaction vessel or release the linkage.

The third invention is a device for measuring chemiluminescence, further including a connection end arrangement body in which the two or more connection ends are arranged along a predetermined course on a predetermined arrangement surface, and a light reception switching mechanism for sequentially guiding light between inside the reaction vessels and the photometer by relatively moving the photometer along the predetermined course, wherein the linkage part moving mechanism is capable of relatively moving the linkage part so as to be sequentially linkable to the two or more reaction vessels through the openings, and front ends of the two or more guiding parts are provided so as to be directly or indirectly in proximity to or in contact with the reaction vessels, and rear ends thereof are provided to the corresponding connection ends.

Here, it is preferable that the two or more reaction vessels, the two or more liquid reception parts, or the like be arranged in a line (column or row) or in a matrix.

The "provided so as to be indirectly in proximity to or in contact with the reaction vessel" includes, for example, a case where the light guiding part is provided via the optical element provided in proximity to the reaction vessel. The optical element may be, for example, a rod lens or an optical fiber.

The "relatively moving the photometer along the predetermined course" includes a case of moving the photometer, a case of moving the connection end arrangement body, and a case of moving both of them. In a case where the photometer is not moved, although the load applied to the photometer will be lowered so as to minimize the influence on the function of the photometer and enhance the reliability, it is necessary to use a flexible member, that is an optical fiber, for the light guiding part at least in part. It is preferable that the "predetermined course" form, for example, a straight line or a smooth curve. It is possible to accumulate the arrangements and facilitate the switching by arranging the connection ends so as to have intervals narrower than those between the adjacent reaction vessels.

Note that it is preferable to additionally include a control part for controlling the linkage part moving mechanism, the reagent injecting mechanism, the shutter or the light reception switching mechanism based on processing contents. The "control part", such as an information processor consisting of a CPU, a program, a memory and the like, a photosensor and a timer, gives instruction to the linkage part moving mechanism and the like in the form of an electrical signal. The processing contents are contents for arrangement or structure of the reaction vessel, the linkage part or the connection end, predetermined measuring time, or chemiluminescent reaction. Here, the "predetermined measuring time" is a period of time in which measurement of chemiluminescence is carried out, and in case of a CLIA assay for example, from injection of the trigger reagent, and in case of an acridinium ester derivative for example, from light emission, measurement is carried out for two seconds (to for five seconds) for example. In case of a CLEIA method, for example, peroxidase is used as a labeled enzyme, and in case of measurement by luminol chemiluminescence, it takes, for example, two minutes from addition of a luminol/hydrogen peroxide solution. The predetermined measuring time depends on sensitivity of the photometer, kind of the substance for chemiluminescence, lifetime of chemiluminescence, amount of the substance for chemiluminescence, for example amount of the trigger reagent, or the like. For example, the predetermined measuring time is a period of time until the lifetime of the chemiluminescence is reached from injection of the reagent for chemiluminescence.

The fourth invention is a device for measuring chemiluminescence, the reagent injecting mechanism injecting the reagent for chemiluminescence through the reagent injection flow channel when or after the shutter brings into a light guiding state to optically connect the photometer to inside the reaction vessel.

This is because such a situation that the shutter has not yet brought into a light guiding state at the moment of chemiluminescence by injection of the reagent for chemiluminescence, e.g., the trigger reagent is prevented.

The fifth invention is a device for measuring chemiluminescence, the light reception switching mechanism optically connecting, depending on the linkage of the linkage part to each of the reaction vessels, each of the connection ends to the photometer correspondingly, and depending on the release of the linkage, releasing the connection.

The "depending on" includes that optical connection is carried out not only interlocking with the linkage of the linkage part to each of the reaction vessels, but also interlocking with a light guiding state brought between the reaction vessel and the connection end, etc. The "optical connection" corresponds to the light guiding state brought by the shutter, and the "releasing the connection" is preferably done after completion of the light shielding state brought by the shutter.

Here, it is preferable that the "nozzle moving mechanism" and the "linkage part moving mechanism" be overlapped at least in part. This is because it is possible to prevent the device size from increasing and make the structure simple. Note that when the nozzle is provided to be movable to the nozzle head, a part of the nozzle moving mechanism is equivalent to the nozzle head moving mechanism.

The sixth invention is a method for measuring chemiluminescence, including the steps of attaching a dispensing tip to a nozzle of a nozzle head, dispensing through the attached dispensing tip a sample solution, a solution of a substance for chemiluminescence or a solution containing magnetic particles capable of having a substance of interest bound, which are each received in a corresponding liquid reception part, causing a magnetic field in the dispensing tip, carrying out suctioning and discharging to separate the magnetic particles to which the substance of interest binds, and dispensing into a reaction vessel a solution containing the labeled substance of interest dissociated from the separated magnetic particles, moving a linkage part relative to the one reaction vessel to link through an opening to the linkage part to form a confined space shielded from external light, switching from a light shielding state to a light guiding state between inside the reaction vessel and a photometer in relation to the linkage of the linkage part to the reaction vessel, measuring an optical state in the reaction vessel by the photometer for a predetermined measuring time, releasing the linkage of the linkage part to the reaction vessel, and switching from the light guiding state to a light shielding state between inside the reaction vessel and the photometer in relation to the release of the linkage of the linkage part to the reaction vessel.

Here, it is preferable that the switching from a light guiding state to a light shielding state be done after the predetermined measuring time passes from injection of the reagent, and before the release of the linkage. The attachment of the dispensing tip to the nozzle is carried out by, for example, causing the nozzle to descend to an opening for attachment of the dispensing tip to fit thereto (see FIGS. 12(a) to 12(c)).

The seventh invention is a method for measuring chemiluminescence, further including the step of injecting a reagent for chemiluminescence into the reaction vessel through a reagent injection flow channel, which is provided to the linkage part, and a front end of which is located inside the reaction vessel by means of the linkage of the linkage part to the reaction vessel, when or after switching from a light shielding state to a light guiding state between inside the reaction vessel and the photometer, the measuring step measuring an optical state in the reaction vessel by the photometer for a predetermined measuring time after injection.

The eighth invention is a method for measuring chemiluminescence, the switching step from a light shielding state to a light guiding state switching from a light shielding state to a light guiding state between the reaction vessel and a connection end corresponding to the reaction vessel arranged along a predetermined course on a predetermined arrangement surface interlocking with the linkage of the linkage part to the reaction vessel, and carrying out an optical connection, depending on the linkage of the linkage part to the reaction vessel, between the corresponding connection end and the photometer, and the switching step from a light guiding state to a light shielding state switching from the light guiding state to a light shielding state between the reaction vessel and the corresponding connection end interlocking with the release of the linkage of the linkage part to the reaction vessel, or releasing the optical connection of the connection end to the photometer.

It is preferable that the switching step be done, as mentioned above, after the predetermined measuring time passes from injection of the reagent.

Advantageous Effects of Invention

According to the first invention or the sixth invention, the linkage part is provided to the nozzle head capable of carrying out automatic attachment of the dispensing tip to the nozzle and dispensing of various kinds of liquids to the liquid reception part, to which nozzle head a magnetic force means capable of separating the magnetic particles is provided. Accordingly, it becomes possible to automatically achieve separation of a substance of interest and measurement of the labeled substance of interest by one device from start to finish. In addition, it is possible to bring into a light guiding state between the reaction vessel and the photometer in relation to the linkage of the linkage part to the reaction vessel, bring into a light shielding state therebetween in relation to the release of the linkage, and inject the reagent for chemiluminescence into the reaction vessel in the linkage. Accordingly, the shielding of the reaction vessel from external light, optical connection to the measuring device, automatic and reliable cooperation with injection of the reagent for chemiluminescence, and automatic and reliable cooperation of release of light shielding of the reaction vessel with light shielding of the photometer are achieved by a simple structure and control. Therefore, it becomes possible to eliminate the need for a dedicated shutter provided to the photometer itself, and quickly, reliably and effectively carry out measurement of chemiluminescence without increasing the device size. In addition, when interlocking the switching of the shutter with linkage or release of the linkage, it becomes possible to carry out processing more quickly.

According to the second invention, the reaction vessel is optically connected to the photometer through the light guiding part, as well as the light guiding part is switched between a light guiding state and a light shielding state by the shutter, so that it is not necessary to provide the shutter for protecting the PMT against noise light in the vicinity of the PMT, and it becomes possible to prevent contamination of the PMT and carry out a reliable measurement.

According to the third invention or the eighth invention, only by sequentially carrying out linkage of the linkage part to the plurality of reaction vessels arranged in a fixed position and release of the linkage, injection of the reagent and measurement by the photometer of chemiluminescence produced in a plurality of reaction vessels will be sequentially carried out interlocking therewith, without carrying the reaction vessels one by one to a position in the vicinity of the photometer, or transferring a solution targeted for measurement to a reaction vessel for exclusive use in photometry provided in the vicinity of the photometer. Accordingly, it becomes possible to quickly and effectively carry out measurement of chemiluminescence.

The fourth invention or the seventh invention is designed such that injection of the reagent for chemiluminescence such as a trigger reagent is carried out when or after the linkage part is connected to each of the reaction vessels, and then a light guiding state is brought between the reaction vessel and the photometer. Accordingly, it becomes possible to reliably measure a chemiluminescent state by the injection of the reagent for chemiluminescence.

The fifth invention or the eighth invention is designed so as to optically connect, depending on linkage of the linkage part to the reaction vessel, the corresponding connection end to the photometer, and depending on release of the linkage, release the connection. Accordingly, with respect to the plurality of reaction vessels, depending on the linkage to each of the reaction vessels through the linkage part, the reaction vessels and the photometer between which confined spaces shielded from external light are formed will be optically connected sequentially, so that it is possible to quickly, effectively and reliably measure the chemiluminescence in the plurality of reaction vessels.

DESCRIPTION OF EMBODIMENTS

Hereinafter, a description is made of a device 10 for measuring chemiluminescence according to a first embodiment of the present invention based on FIGS. 1 to 4(b).

Figure 1:
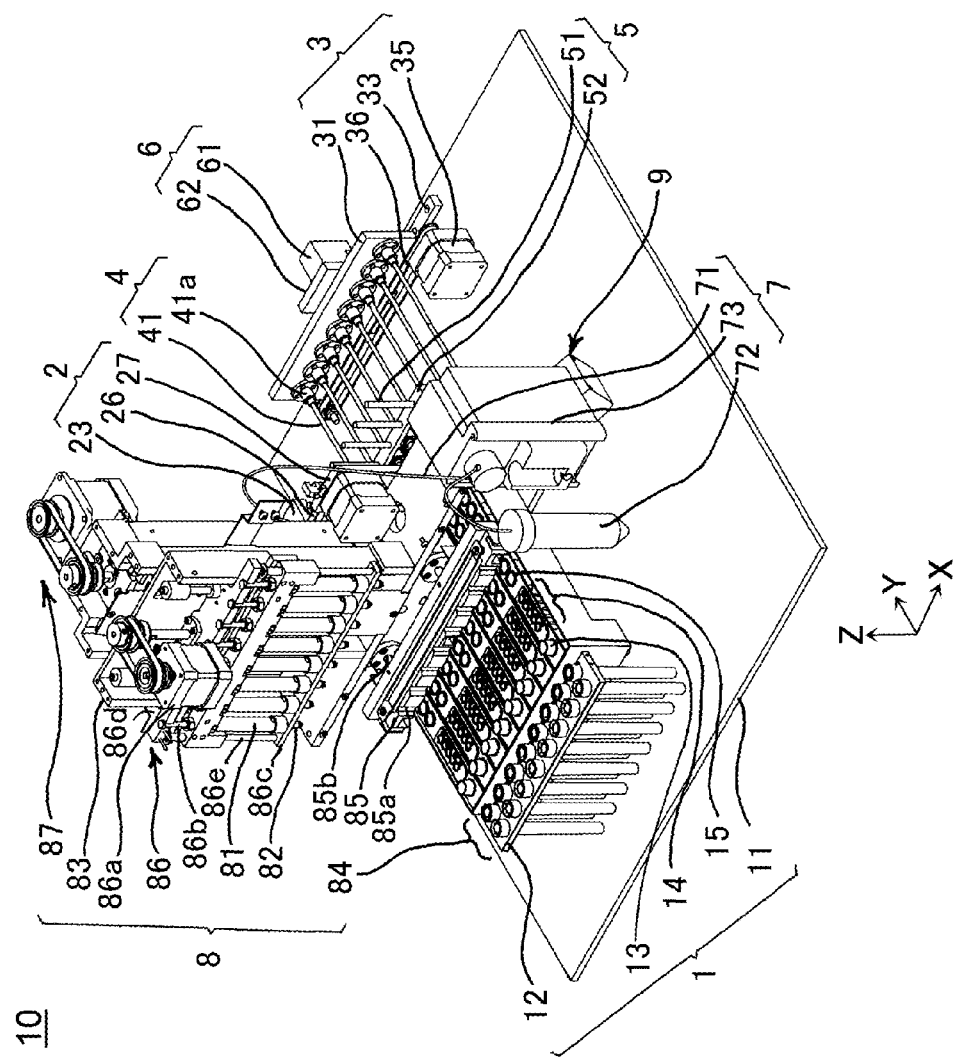
FIG. 1 is a front perspective view showing almost the whole of a device for measuring chemiluminescence according to a first embodiment of the present invention.
Figure 2:
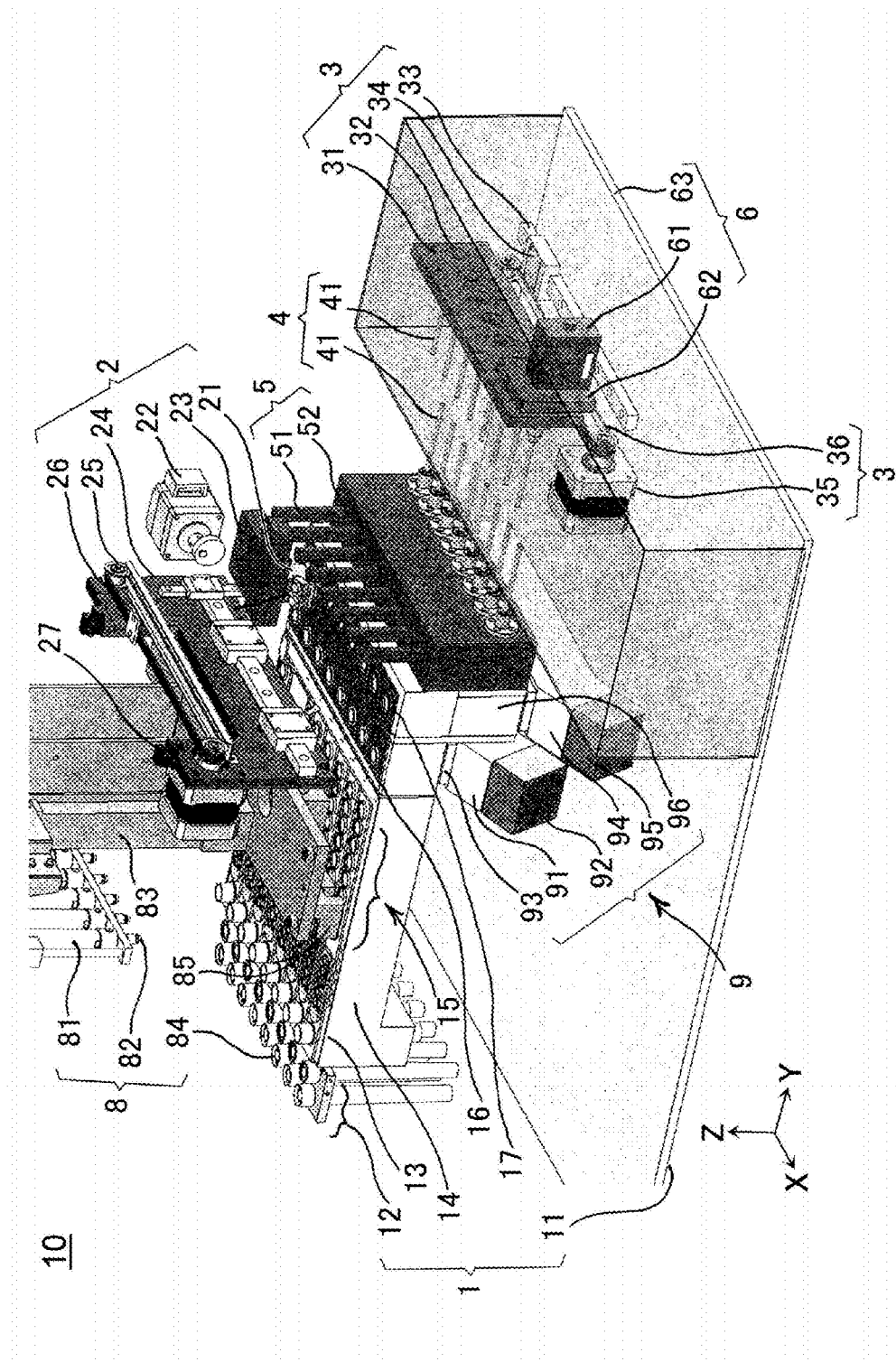
FIG. 2 is a partially enlarged back perspective view of the device shown in FIG. 1.

In FIGS. 1 and 2, almost the whole of the device 10 for measuring chemiluminescence is shown. A plurality of the devices 10 for measuring chemiluminescence are fixedly provided on a stage 11, and include a vessel group 1 having a plurality of translucent reaction vessels 16, 17 (in this example, eight in each) (the volume being, for example, approximately 500 μL and approximately 1 mL in each), a linking mechanism 2 having a linkage part moving mechanism 22 to 29 by which a linkage part 21 linkable to the reaction vessels 17 through openings 17a thereof is movably provided with respect to the vessel group 1, a connection end arrangement body 3 in which a plurality of (in this example, eight) connection ends 32 are arranged along a predetermined course on a predetermined arrangement board 31, and a plurality of (in this example, eight) light guiding parts 4, each of the front ends of which is provided so as to be indirectly in proximity to or in contact with each of the plurality of (in this example, eight) reaction vessels 17 for photometry belonging to the vessel group 1 and each of the rear ends of which is provided at the connection end 32.

Furthermore, the device 10 for measuring chemiluminescence includes a shutter 5 for bringing into a light guiding state interlocking with the linkage of the linkage part 21 to the reaction vessel 17 and bringing into a light shielding state interlocking with the release of the linkage of the inside of each of the reaction vessels 17 to each of the corresponding connection ends 32, a photometer 6, a trigger reagent injecting mechanism 7 having a trigger reagent injection flow channel 71 capable of injecting a trigger reagent when the front end thereof is located inside the reaction vessel 17 by means of the linkage of the linkage part 21 to the reaction vessel 17, a nozzle head 8 for carrying out treatments such as extracting a substance of interest from a sample solution extracted from a patient with the use of magnetic particles, labeling the substance of interest with a substance for chemiluminescence, for example an acridinium-labeled antibody, and dispensing the solution to be targeted for measurement into the reaction vessels 17, and a temperature controller 9 for carrying out temperature control by receiving the whole of the reaction vessels 16, 17 in temperature control blocks 93, 96 having a light shielding property.

Next, a detailed description of these components is further made based on the drawings.

As mainly shown in FIGS. 1 and 2, the vessel group 1 of the device 10 for measuring chemiluminescence provided to the nozzle head 8 includes, in addition to the reaction vessels 16, 17, for example, a plurality of (in this example, eight) sample reception parts 13 each for receiving a sample such as serum collected from a patient, a tip rack 12 for receiving a plurality of (in this example, sixteen) dispensing tips 84 to be attached to a nozzle 82 mentioned below in an attachable state by means of the descent of the nozzle 82, reagent reception parts 14 for receiving various reagents including a magnetic particle suspended solution containing magnetic particles for extracting a substance of interest to be targeted for measurement from the sample solution, a washing solution, a dissociating solution, as a substance for chemiluminescence, for example, an acridinium-labeled antibody, a trigger reagent (e.g., $H_2O_2$) and an NaOH solution, or the like, and liquid reception parts 15 for carrying out reception of the other reagents, mixing of the sample solution with the reagent or the like. Here, the plurality of reagent reception parts 14 arranged in the Y-axis direction (in this example, five in the Y-axis direction), the plurality of (in this example, eight) reagent reception parts 14 and the liquid reception parts 15 are provided in a cartridge vessel extending in the Y-axis direction. Accordingly, the eight cartridge vessels are being arranged in total in the X-axis direction.

The linking mechanism 2 of the device 10 for measuring chemiluminescence includes one linkage part 21 which is sequentially linked to the eight reaction vessels 17 for photometry through openings 17a thereof to form a confined space shielded from external light, a board 23 under which the linkage part 21 is provided and to which a Z-axis moving mechanism mentioned below or the like is provided, and a linkage part moving mechanism 24 to 29 capable of moving the linkage part 21 relative to the reaction vessels 17. The linkage part moving mechanism 24 to 29 includes an X-axis moving mechanism for moving the linkage part 21 (or the board 23) in the X-axis direction (the column direction of the reaction vessels 17), a Z-axis moving mechanism for moving the linkage part 21 in the Z-axis direction (the vertical direction), and a Y-axis moving mechanism (not shown) for moving the linkage part 21 in the Y-axis direction (the row direction).

Figure 3:
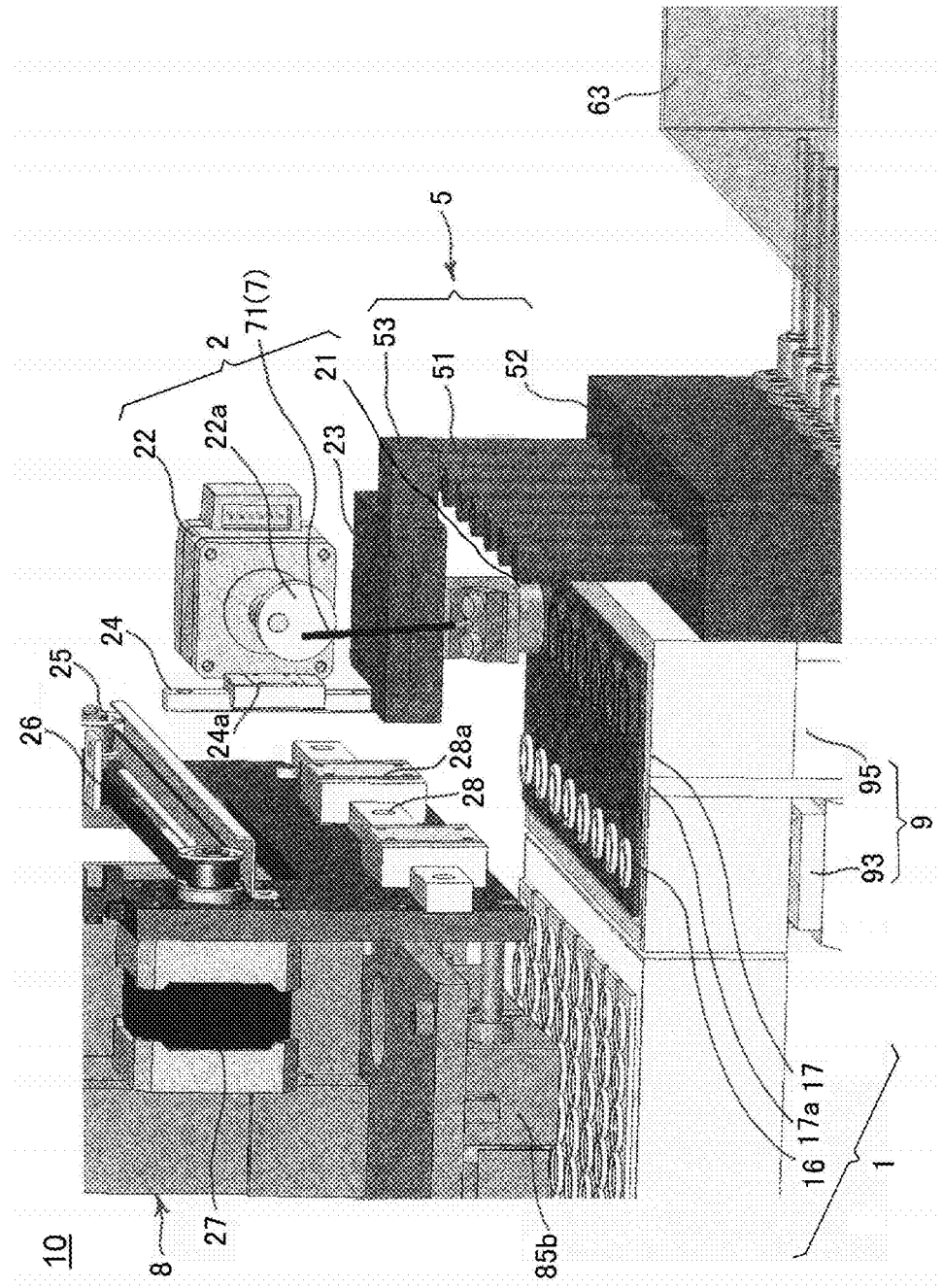
FIG. 3 is a partially enlarged back perspective view of the device shown in FIG. 2.
Figure 4:
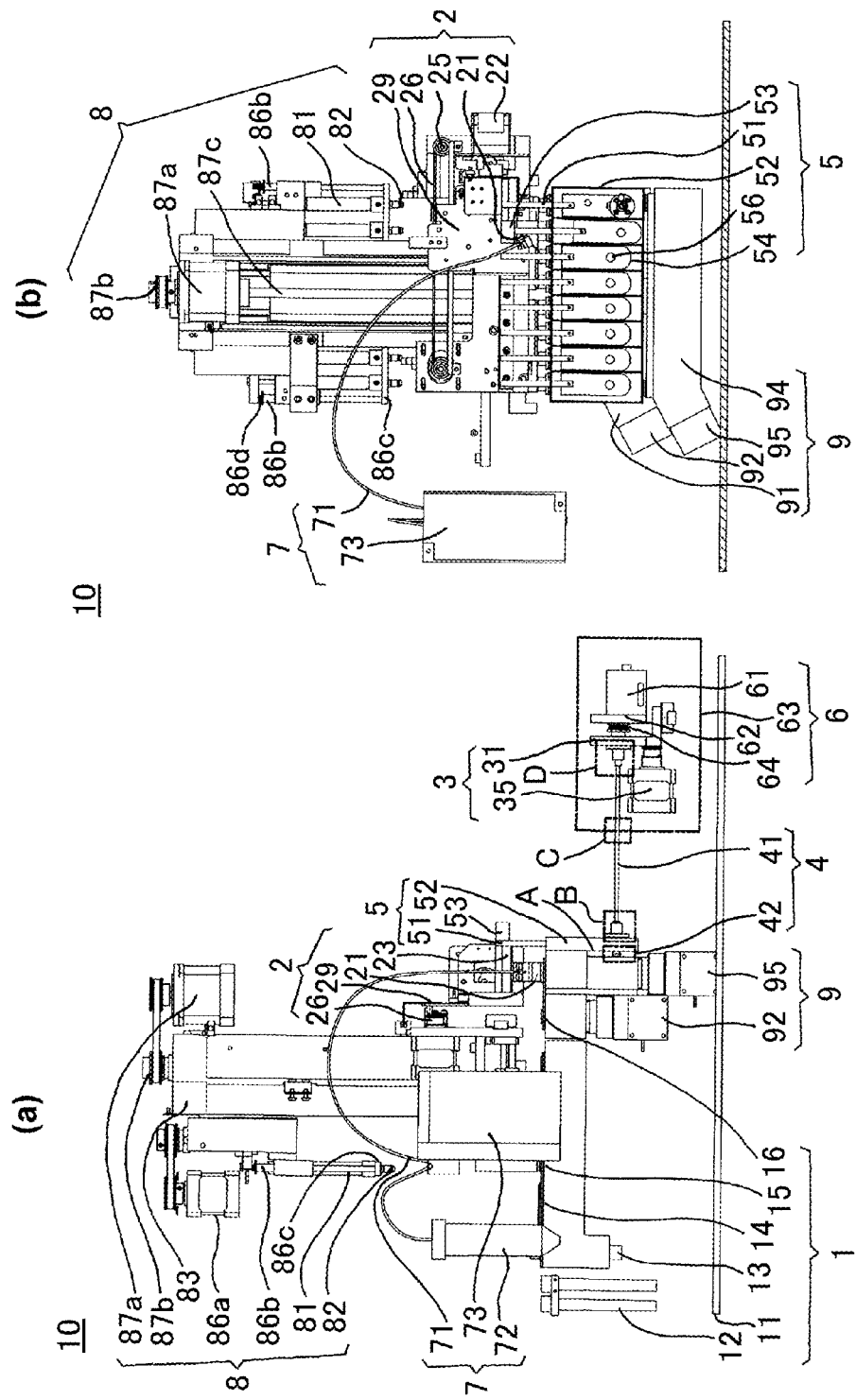
FIGS. 4(a) and 4(b) are a side view of the device shown in FIG. 1 and a partially cutaway front view showing the device shown in FIG. 1.

As mainly shown in FIG. 3, the X-axis moving mechanism includes an X-axis moving motor 27, two pulleys 25, one of which is driven by the motor 27, a timing belt 26 extended between the two pulleys 25, an X-axis guide rail 28, a guide member 28a which is engaged with the X-axis guide rail 28 so as to be guided, and an X-axis moving frame body 29 (see FIGS. 4(a) and 4(b)) to which the guide member 28a is attached and which is attached to the board 23 by which the linkage part 21 is movably supported in the Z-axis.

The X-axis moving frame body 29 is provided with the board 23, that is, the Z-axis moving mechanism for moving the linkage part 21 in the vertical direction (the Z-axis direction). The Z-axis moving mechanism includes a Z-axis moving motor 22 attached to the X-axis moving frame body 29, a timing belt (not shown) driven through a pulley 22a provided to the motor 22, a guide member 24a attached to the board 23 which is fixed to the timing belt and moves in the vertical direction, and a Z-axis guide rail 24 (see FIGS. 2 and 3) attached to the X-axis moving frame body 29 for guiding the guide member 24a.

Note that the movement of the linkage part 21 in the Y-axis direction (the row direction of the reaction vessels 16, 17) is carried out with the use of the Y-axis moving mechanism of a nozzle moving mechanism mentioned below for moving the nozzle head 8 in the Y-axis direction.

The board 23 of the linkage part 21 is provided with a pressing part 53 for sequentially pressing eight rods 51 provided to the shutter 5 depending on the linkage of the linkage part 21 to each of the reaction vessels 17, and sequentially releasing the press depending on the release of the linkage. The pressing part 53 is formed so as to project from the board 23 toward the side provided with the shutter 5. The linkage part 21 has a fitting part, the lower part of which is designed to fit into each of the openings 17a of the reaction vessel 17, and the upper part of which is provided with a reagent injection flow channel 71 which passes through an upper side board of the linkage part 21 capable of dispensing a trigger reagent when the front end thereof is located inside the reaction vessel 17 by means of the linkage of the linkage part 21 to the reaction vessel 17. The reagent injection flow channel 71 is formed of a flexible resin having a light shielding property. In addition, the fitting part is provided with a packing having a light shielding property, or the like. In addition, the reaction vessels 17, the linkage part 21, the shutter 5 and a PMT 61 are individually formed of a member having a light shielding property, coated with a light shielding membrane, or received in a dark room or a dark box.

The portion corresponding to reference sign 3 of the device 10 for measuring chemiluminescence is a connection end arrangement body and light reception switching mechanism 3 in which a plurality of (in this example, eight) connection ends 32, a connection end arrangement body having the arrangement board 31, arranged on a horizontal straight line as the predetermined course, on which the connection ends 32 are arranged at predetermined intervals (for example, intervals between the adjacent reaction vessels 17), and a light reception switching mechanism for relatively moving the arrangement board 31 so that the PMT 61 of the photometer 6 fixed to the stage 11 passes the predetermined course on which the connection ends 32 are arranged are included. The light reception switching mechanism includes a motor 35 for moving the arrangement board 31 along the X-axis direction (the column direction of the reaction vessels 17), a timing belt 36 driven by the motor 35, a guide rail 33 for guiding the movement of the arrangement board 31, and a guide member 34 which is guided by the guide rail 33 and movably supports the arrangement board 31. The movement of the linkage part 21 synchronizes with the movement of the PMT 61.

The connection end arrangement body and light reception switching mechanism 3 is received in a dark box 63 together with the PMT 61 of the photometer 6.

The light guiding parts 4 of the device 10 for measuring chemiluminescence include a plurality of (in this example, eight) rod lenses 42, the front end of which is in proximity to the side of each of the translucent reaction vessels 17 and passes through each of the temperature control blocks 96 having a light shielding property, and the rear end of which is provided in proximity to each of a plurality of (in this example, eight) opening/closing plates 54 (see FIG. 4(b)) of the shutter 5, and eight flexible optical fibers 41, the front end of which is provided in proximity to each of the plurality of (in this example, eight) opening/closing plates 54 of the shutter 5, and the rear end of which is provided to each of the connection ends 32. The optical fiber 41 will flex in association with the movement of the connection end arrangement board 31 (Note that, in FIGS. 2 and 3, although the optical fiber 41 is drawn such that the middle part thereof is omitted, it goes without saying that the eight optical fibers 41 are linked in the same arrangement order without intersecting to each other, as shown in FIGS. 1, 4(a) and 4(b)). As shown as reference signs A, B, C, and D in FIG. 4(a), the rod lens 42, the optical fiber 41 and the connection part to each unit are light shielded by rubber or the like.

The shutter 5 of the device 10 for measuring chemiluminescence is provided with, as mainly shown in FIGS. 1 to 3, the eight rods 51 which are provided so as to be, by means of the linkage of the linkage part 21 to the reaction vessel 17, movable in the downward direction in association with the descent of the pressing part 53 formed to the board 23 provided with the linkage part 21 and restorable to the original reference position after the press by the pressing part 53 is released, a light shielding case 52 for shielding external light, and the plurality of (in this example, eight) optical fibers 41 provided so as to project from the side board of the light shielding case 52.

In FIG. 4(b), as shown in a state where the side board of the shutter 5 is removed, each of the eight rods 51 is provided to each of a plurality of (in this example, eight) compartments which are partitioned within the light shielding case 52 in a light shielding state. Note that, in the drawing, the right-end compartment has a fastener position for the optical fiber 41 illustrated, and the second compartment from the right end shows a state where the rod 51 is pressed by the pressing part 53 provided to the board 23.

Each of the rods 51 is coupled to the opening/closing plate 54 formed of a non-translucent member in each of the compartments of the light shielding case 52. The opening/closing plate 54 is movable in the downward direction when the rod 51 is pressed, and is always biased upwardly by a spring (not shown) provided in each of the compartments so as to be restorable to the original reference position after the press by the rod 51 is released.

The opening/closing plate 54 is provided with a shutter hole 56, which, when the rod 51 is at the reference position, brings into a light shielding state between the optical fiber 41 and the rod lens 42, or when the rod 51 is pressed to descend to an elevation where the optical fiber 41 and the rod lens 42 are provided, brings into alight guiding state between the optical fiber 41 and the rod lens 42. As mentioned above, it is shown in FIG. 4(b) that one of the eight rods 51 is pressed so that the shutter hole 56 descends to the neighboring fiber position, thereby bringing the light guiding part into a light guiding state.

The photometer 6 of the device 10 for measuring chemiluminescence includes the photomultiplier tube (PMT) 61 for multiplying photoelectrons which are excited by inputted light, a filter 62 through which only light in a predetermined wavelength range passes, a dark box 63 for placing the connection end arrangement body and light reception switching mechanism 3 along with the PMT 61 in a light shielded atmosphere, and an optical element 64, such as a rod lens, which is optically connected to a connection end 32 provided to the connection end arrangement board 31 so as to receive light. The PMT 61 is fixedly provided to the dark box 63.

The reagent injecting mechanism 7 of the device 10 for measuring chemiluminescence includes a reagent injection flow channel 71 capable of dispensing a trigger reagent as the reagent for chemiluminescence, the front end of which is located inside the reaction vessel 17 by means of the linkage of the linkage part 21 to the reaction vessel 17, a reagent reception part 72 for receiving the trigger reagent, and a pump mechanism 73 for transferring and injecting the trigger reagent from the reagent reception part 72 through the flow channel 71 into the reaction vessel 17. The trigger reagent reception parts 72 and the pump mechanism 73 are provided to the nozzle head 8. Accordingly, it is preferable that the flow channel 71 have flexibility so as to be deformable depending on the movement of the linkage part 21.

The nozzle head 8 of the device 10 for measuring chemiluminescence is provided with a plurality of (in this example, eight) cylinders 81 included in a suctioning and discharging mechanism 86 for carrying out suctioning and discharging of gas, a plurality of (in this example, eight) nozzles 82 which are in communication with the cylinders 81, and to the front ends of which, dispensing tips 84 for carrying out suctioning and discharging of liquid are attachable, and a magnetic force means 85 capable of causing a magnetic field inside the dispensing tips 84 attached to the nozzles 82. Here, reference sign 83 represents a frame body for supporting the nozzles and the like from the upper side.

The dispensing tips 84 are received in the tip rack 12 in a state where the plurality thereof (in this example, sixteen) are attachable to the lower ends of the nozzles 82. The suctioning and discharging mechanism 86 further includes, in addition to the cylinders 81, a detaching plate driving pin 86e for driving a detaching plate 86c for the dispensing tips 84 or the like, to which a plurality of (in this example, eight) piston rods 86b of the cylinders 81 are attached, and a motor 86a for moving upwardly and downwardly a plate 86d for suctioning and discharging, which allows descending a predetermined distance from a suctioning and discharging area of a liquid, engaging at the descended position and moving further in the downward direction. The upper portion of the nozzle 82 is provided with the detaching plate 86c through which a plurality of (in this example, eight) holes for detachment are provided, the inner diameter of which holes is larger than the outer diameter of the nozzle 82 but is smaller than the outer diameter of the dispensing tip 84, so that each of the nozzles 82 passes therethrough. Accordingly, the driving in the downward direction by the plate 86d for suctioning and discharging allows the dispensing tip 84 to be detached from the nozzle 82.

In addition, the nozzle head 8 includes, as a nozzle moving mechanism, a Z-axis moving mechanism 87 for moving the nozzle 82 in the Z-axis direction and a Y-axis moving mechanism for moving the nozzle 82 in the Y-axis direction. Note that the nozzle 82 is not moved in the X-axis direction in this example. The Z-axis moving mechanism 87 includes a motor 87a, a rotor 87b which is rotationally driven by the motor 87a, and a ball screw 87c which is rotationally driven by means of the rotation of the rotor 87b, in which the frame body 83 is attached to a nut part into which the ball screw 87c is screwed, so that the frame body 83 is moved upwardly and downwardly. Note that the Y-axis moving mechanism for moving the nozzle head 8 with respect to the vessel group 1 in the Y-axis direction may be activated, as described in the Z-axis moving mechanism 87, by providing the nozzle head 8 having a ball screw disposed along the Y-axis direction, a motor for rotationally driving the ball screw, and a nut part into which the ball screw is screwed. The Y-axis moving mechanism provides the movement of the linkage part in the Y-axis direction.

The magnetic force means 85 has a plurality of (in this example, eight) permanent magnets 85a arranged on a magnet arrangement member in a line at the same intervals as those among the nozzles 82 along the X-axis direction. The magnet arrangement member is provided so as to come close to and separate from the dispensing tip 84 attached to the nozzle 82 by the actuator 85b.

The temperature controller 9 of the device 10 for measuring chemiluminescence separately carries out collective temperature control of the plurality of (in this example, eight) reaction vessels 16 and the plurality of (in this example, eight) reaction vessels 17. The reaction vessels 16 are provided with a temperature control block 93, a Peltier element 91 and a fan and fin 92, whereas the reaction vessels 17 are provided with a temperature control block 96, a Peltier element 94 and a fan and fin 95.

Next, a description is made of the motion of the device 10 for measuring chemiluminescence according to the embodiments.

A description is made of a case of preparing a tracer in immunoassay by directly labeling an antigen substance or an antibody substance as the substance of interest in serum with the use of an acridinium ester derivative as a compound for chemiluminescence method.

In step S1, a serum sample solution collected from each of eight patients is received in each of the sample reception parts 13.

In step S2, moving the nozzles 82 of the nozzle head 8 by the Y-axis moving mechanism to the larger position in the Y coordinate of the tip rack 12 and causing the nozzles 82 to descend along the Z-axis direction allow the eight dispensing tips 84 to be attached to the nozzles 82. With the use of the dispensing tips 84, for example, 0.1 mL of the serum sample solutions are suctioned from the sample reception parts 13, and discharged into the liquid reception parts 15 all at once.

In step S3, moving the nozzle head 8 in the Y-axis direction and causing the piston rods 86b to descend beyond a certain level by the motor 86a for suctioning and discharging provided to the nozzle head 8 allow the eight dispensing tips 84 contaminated with the sample to be detached at the original position in the tip rack 12 by a member for tip detachment provided to the upper portion of the nozzles 82. The new dispensing tips 84 are attached which have been received at the smaller position in the Y coordinate of the tip rack 12. Then, the nozzle head is moved in the Y-axis direction to suction 0.1 mL of an acridinium-labeled antibody received in any of the reagent reception parts 14, and is moved in the Y-axis direction to the eight liquid reception parts 15 to discharge the same, followed by incubation at room temperature for 120 minutes.

In step S4, moving the nozzle head 8 along the Y-axis, in order to examine the antigen substance in the serum targeted for measurement, moving the dispensing tips 84 attached to the nozzle 82 above any of the reagent reception parts 14 in which the magnetic particle suspension is received in which the magnetic particles, onto the surface of which the antibody capable of specifically binding to the antigen substance is fixed, are suspended, causing the dispensing tips 84 to descend with the use of the Z-axis moving mechanism 87, inserting the front ends of the dispensing tips 84 inside the reagent reception parts 14, suctioning 0.5 mL of the received magnetic particle suspension in the dispensing tips 84, causing the dispensing tips 84 to ascend with the use of the Z-axis moving mechanism 87, moving the dispensing tips 84 in the liquid reception parts 15 by the Y-axis moving mechanism, causing the dispensing tips 84 to descend with the use of the Z-axis moving mechanism 87, discharging the suspension into the liquid reception parts 15 while moving the piston rods 86b upwardly and downwardly, and repeating the suctioning and discharging result in stirring.

In step S5, incubating the suspension in the liquid reception parts 15 at room temperature for 30 minutes allows the antigen substance as the substance of interest labeled with the acridinium-labeled antibody in the sample solutions to bind and fix to the magnetic particles.

In step S6, in a state of bringing the dispensing tips 84 to a standstill at a predetermined height position by the Z-axis moving mechanism 87 and causing the magnets 85a to come close to each of the dispensing tips 84 all at once with the use of the magnetic force means 85, repeating the suctioning and discharging by moving the plate for suctioning and discharging upwardly and downwardly allows the magnetic particles which have captured the labeled substance of interest to be attracted to the inner wall of the dispensing tips 84 for separation. Moving the nozzle head 8 by the Y-axis moving mechanism with the magnets 85a being close to the dispensing tips 84 so as to be located above the reagent reception parts 14 in which the washing solution is received, causing the dispensing tips 84 to descend by the Z-axis moving mechanism 87, and, in a state where the magnets 85a are separated, repeating the suctioning and discharging allow washing, so that B/F separation is carried out.

In step S7, in a state where the magnetic particles are attracted to the inner wall again by causing the magnets 85a of the magnetic force means 85 to come close to the dispensing tips 84, moving the dispensing tips 84 by the Y-axis moving mechanism to the reaction vessels 17 in which, for example, 0.1 mL of water is received, inserting the dispensing tips 84 into the reaction vessels 17 by the Z-axis moving mechanism 87, re-suspending the magnetic particles in the liquid in a state where the magnets 85a are separated allow the labeled substance of interest to be dissociated from the magnetic particles, followed by removal of the magnetic particles.

In step S8, driving the X-axis moving motor 27 of the linkage part moving mechanism causes the linkage part 21 to move along the X-axis so as to locate above the first reaction vessel 17, and then causing the linkage part 21 to descend by the Z-axis moving motor 22 of the Z-axis moving mechanism or the like allow the fitting part thereof to fit into the opening 17a of the reaction vessel 17, thereby forming a confined space shielded from external light in combination with the reaction vessel 17. In doing so, the pressing part 53 provided to the board 23 is on the rod 51 of the shutter 5 corresponding to the reaction vessel 17 that the linkage part 21 is going to link to, which pressing part 53 descends interlocking with the descent of the linkage part 21 so as to press down the opening/closing plate 54 bound to the rod 51 in the compartment by means of the linkage of the linkage part 21, so that the shutter hole 56 provided through the opening/closing plate 54 brings into a light guiding state between the rod lens 42 provided in proximity to the side surface of the reaction vessel 17 and the optical fiber 41, and thus brings into a light guiding state from inside the reaction vessel 17 to the connection end 32.

In step S9, the connection end arrangement board 31 moves along the X-axis such that the PMT 61 of the photometer 6 is optically connected to the connection end 32 corresponding to the reaction vessel 17 to which the linkage part 21 links in synchronization with the linkage through the opening 17a of the reaction vessel 17 of the linkage part 21. Accordingly, the linkage of the linkage part 21 through the opening of the reaction vessel 17 brings into a light guiding state from inside the reaction vessel 17 to the PMT 61.

In step S10, through the reagent injection flow channel 71, which is provided to the linkage part 21, and the front end of which is located inside the reaction vessel 17 by means of the linkage to the reaction vessel 17, 0.2 mL of $H_2O_2$, which is a trigger reagent, and 0.2 mL of 0.2 N NaOH are injected into the reaction vessel 17, so that chemiluminescence is produced, and light receiving will be carried out by the PMT 61 for a predetermined measuring time.

After the predetermined measuring time passes, the linkage part 21 ascends, the opening/closing plate 54 coupled to the rod 51 ascends in the compartment interlocking with the ascent of the linkage part 21, and the shutter hole 56 provided through the opening/closing plate 54 ascends, so that a light guiding state is brought between the rod lens 42 and the optical fiber 41, and the linkage part 21 will be separated from the first reaction vessel 17 and move to the second reaction vessel 17. Also for the second reaction vessel 17, the same treatment as for the first reaction vessel will be carried out. In this way, the treatments are sequentially carried out for the eight reaction vessels 17.

Hereinafter, a description is made of a device 100 for measuring chemiluminescence according to a second embodiment of the present invention based on FIGS. 5 to 12(c).

Figure 5:
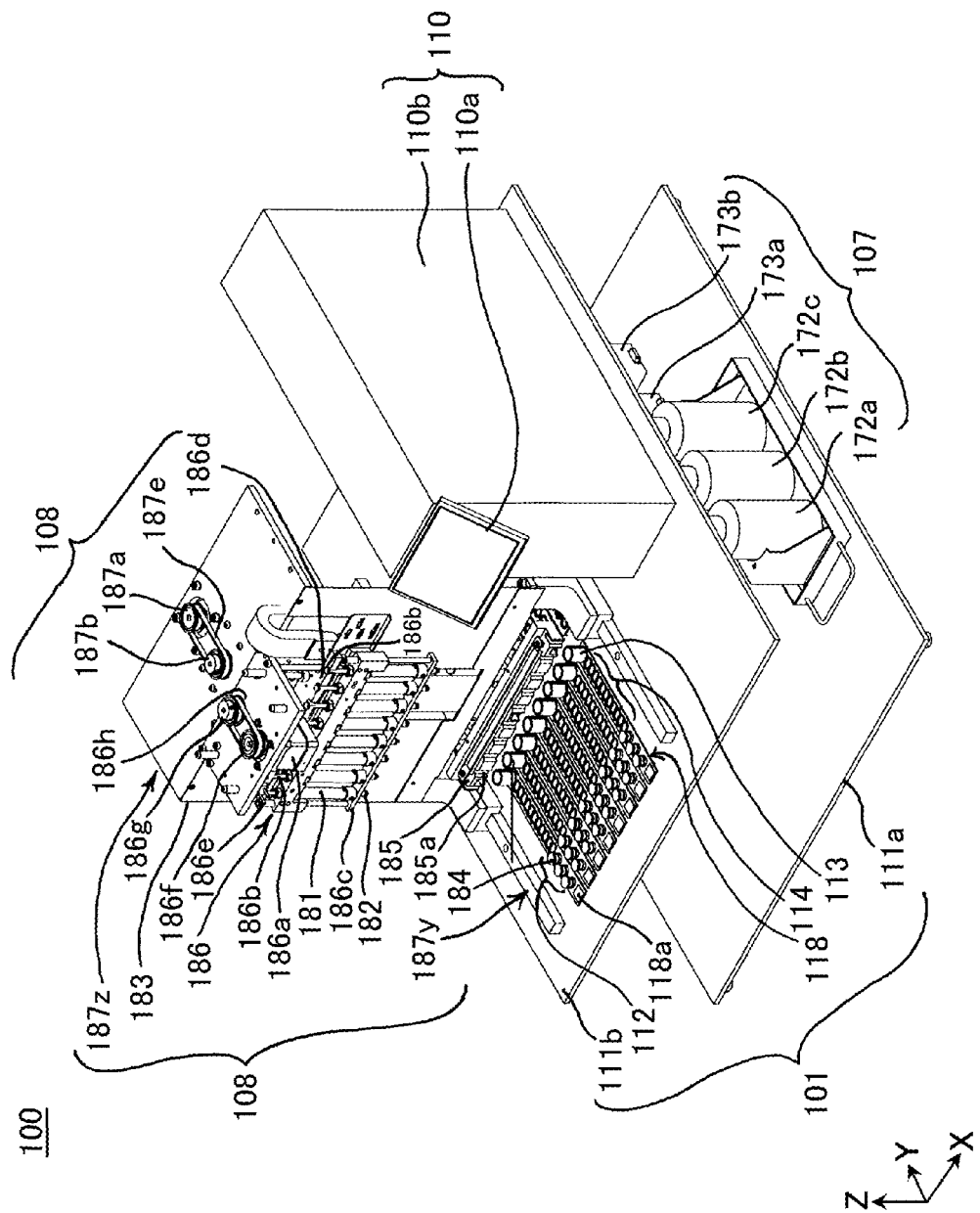
FIG. 5 is a front perspective view showing almost the whole of a device for measuring chemiluminescence according to a second embodiment of the present invention.
Figure 6:
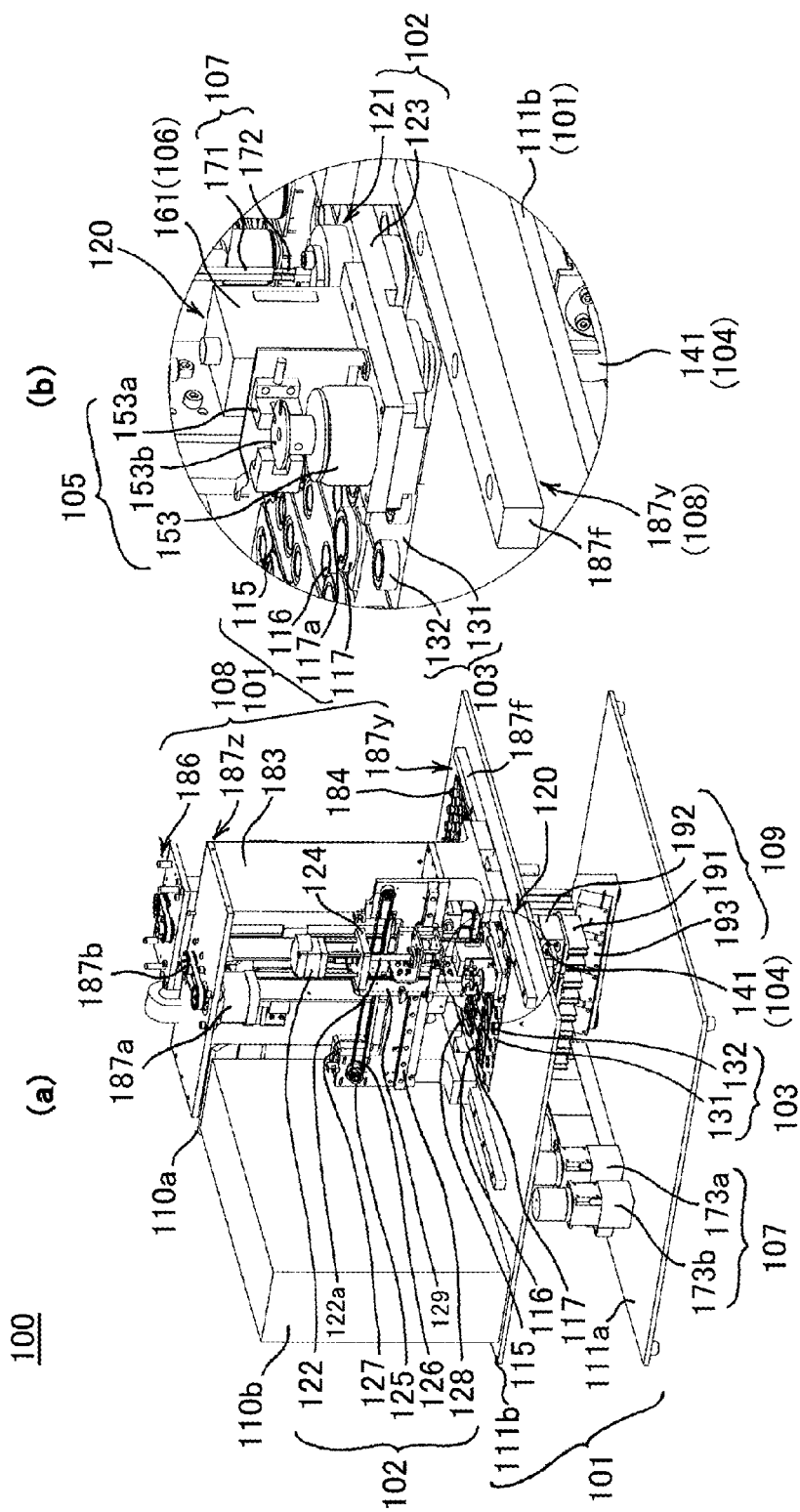
FIGS. 6(a) and 6(b) are a back perspective view of the device shown in FIG. 5 and a partially enlarged perspective view thereof.
Figure 7:
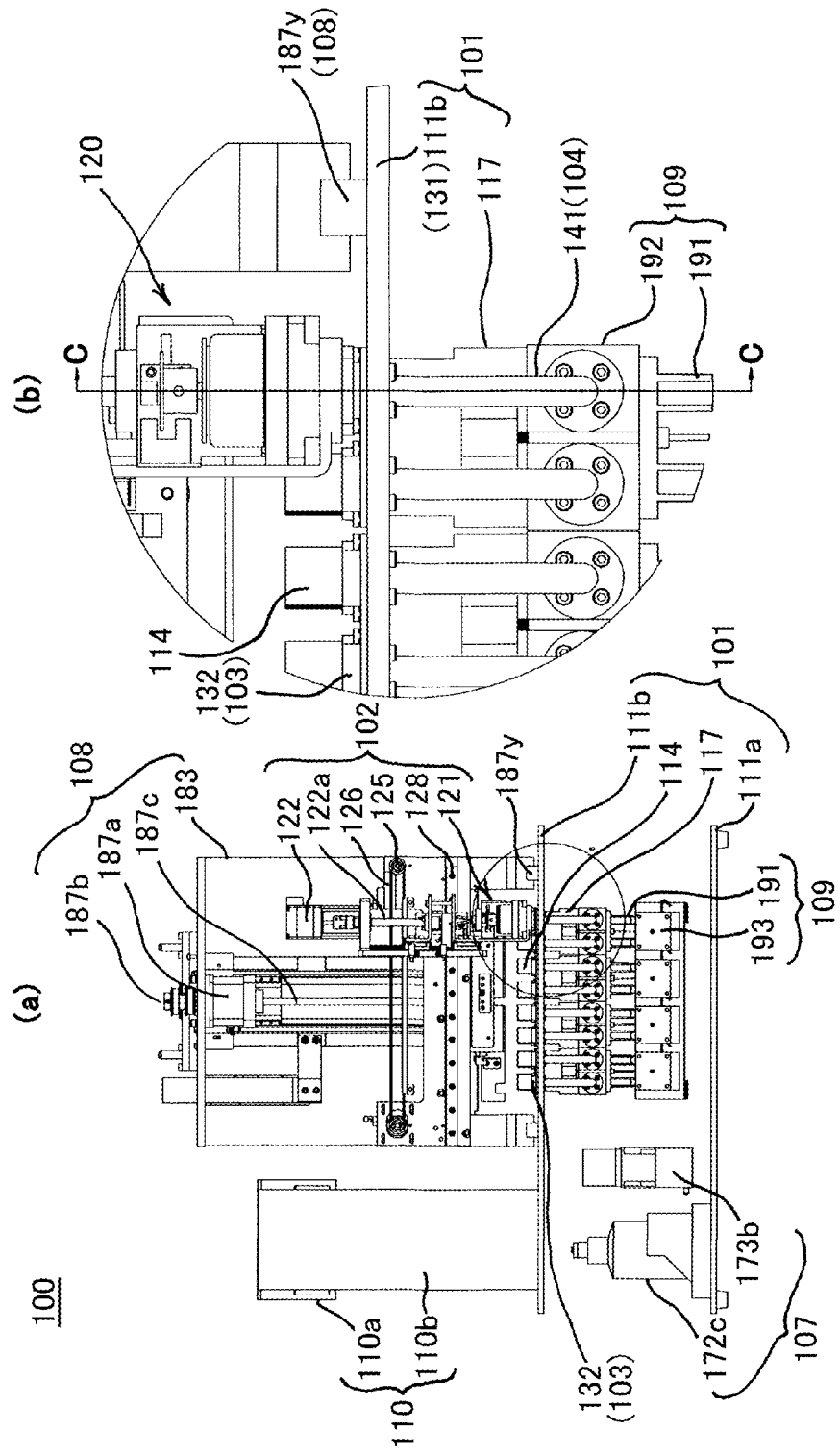
FIGS. 7(a) and 7(b) are a back view of the device shown in FIG. 5 and a partially enlarged view thereof.

FIGS. 5, 6(a) and 6(b) show almost the whole of the device 100 for measuring chemiluminescence. The device 100 for measuring chemiluminescence is fixedly provided to a stage 111b, and includes a vessel group 101 having a plurality of translucent reaction vessels 116, 117 (in this example, eight in each) (the volume being, for example, 500 μL and approximately 1 mL in each, see FIGS. 6(a) and 6(b)), a linking mechanism 102 having a linkage part moving mechanism 122 to 129 by which a linkage part 121 linkable to the reaction vessels 117 through openings 117a thereof (see FIGS. 12(a) to 12(c) in detail) is movably provided with respect to the vessel group 101, a connection end arrangement body 103 in which a plurality of (in this example, eight) connection ends 132 are arranged along a predetermined course (a linear course extending in the X-axis direction) on a predetermined arrangement board 131 (which may serve as a stage 111b), a light guiding part 104 consisting of a plurality of (in this example, eight) optical fibers 141, each of the front ends of which is provided so as to be indirectly in proximity to or in contact with each of the plurality of (in this example, eight) reaction vessels 117 for measurement belonging to the vessel group 101 and each of the rear ends of which is provided at the connection end 132, and a photometer 106 having a PMT (photomultiplier tube) 161.

Furthermore, the device 100 for measuring chemiluminescence includes a shutter 105 for bringing into a light guiding state interlocking with the linkage of the linkage part 121 to the reaction vessel 117 and bringing into a light shielding state before the linkage is released and after the reagent for chemiluminescence is dispensed and then the predetermined measuring time passes between each of the connection ends 132 and the PMT 161, a trigger reagent injecting mechanism 107 by which a trigger reagent as a reagent for chemiluminescence may be injected when the front end thereof is located inside the reaction vessel 117 by means of the linkage of the linkage part 121 to the reaction vessel 117 and the trigger reagent is transferred by pumps 173a, 173b when the rear end thereof is in communication with trigger reagent reception parts 172a, 172b, 172c, a nozzle head 108 having a plurality of (in this example, eight) nozzles 182 for carrying out treatments such as extracting a substance of interest from a sample solution extracted from a patient with the use of magnetic particles, labeling the substance of interest with a substance for chemiluminescence, for example an acridinium-labeled antibody, and dispensing a labeled substance of interest-containing solution in which the labeled substance of interest to be targeted for measurement is re-suspended into the reaction vessels 117 or the like to which nozzles 182 dispensing tips 184a are attachable, and a temperature controller 109 for carrying out temperature control by receiving each of the reaction vessels 116, 117 in a temperature control block 192 having a light shielding property and being provided with a fin 191 which is coolable by a blower 193.

Next, a detailed description of each of these components of the device 100 for measuring chemiluminescence is further made based on the drawings.

As mainly shown in FIGS. 5, 6(a) and 6(b), the vessel group 101 includes, in addition to the reaction vessels 116, 117, for example, a plurality of (in this example, eight) sample reception parts 113 each for receiving a sample such as serum collected from a patient, reagent reception parts 112 each for receiving a lyophilized reagent, tip reception parts 115 for receiving the plurality of (in this example, thirty-two) dispensing tips 184a or the like in an attachable state by means of the descent of the nozzle 182, reagent and solution reception parts 114 for receiving various reagents including a magnetic particle suspension containing magnetic particles for extracting a substance of interest to be targeted for measurement from the sample solution, a washing solution, a dissociating solution, as a substance for chemiluminescence, for example, an acridinium-labeled antibody, a trigger reagent (e.g., $H_2O_2$) and an NaOH solution, and the like. Here, the sample reception parts 113 arranged in the Y-axis direction, the plurality of (in this example, three in the Y-axis direction) lyophilized reagent reception parts 112, and the plurality of (in this example, eleven in the Y-axis direction) reagent and solution reception parts 114 are provided to eight first cartridge vessels 118 (see FIGS. 11(a) and 11(b)) being arranged in the X-axis direction and extending in the Y-axis direction, and the reaction vessels 116, 117 and the plurality of (in this examples, four) tip reception parts 115 which are also arranged in the Y-axis direction are provided to eight second cartridge vessels 119 (see FIGS. 12(a) to 12(c)) arranged in the X-axis direction. Note that reference sign 118a represents cord data encompassing sample information and examination information about the first cartridge vessel 118.

The linking mechanism 102 of the device 100 for measuring chemiluminescence includes one linkage part 121 which is sequentially linked to the eight reaction vessels 117 for measurement through openings 117a thereof to form a confined space shielded from external light, a board 123 on which the linkage part 121, the shutter 105 and the photometer 106 are provided and which is movably supported in the Z-axis direction by a linkage part Z-axis moving mechanism mentioned below, and a linkage part moving mechanism 122, 124 to 129 capable of moving the linkage part 121 (or the board 123, that is, a detection part 120 having the shutter 105 and the photometer 106 combined) relative to the reaction vessels 117. The linkage part moving mechanism 122, 124 to 129 includes a linkage part X-axis moving mechanism for moving the linkage part 121 (that is, the board 123 and the like) in the X-axis direction (the column direction of the reaction vessels 117), a linkage part Z-axis moving mechanism for moving the linkage part 121 in the Z-axis direction (the vertical direction), and a linkage part Y-axis moving mechanism for moving the linkage part 121 in the Y-axis direction (the row direction).

As mainly shown in FIG. 6(a), the linkage part X-axis moving mechanism includes a linkage part X-axis driving motor 127, two pulleys 125, one of which is driven by the motor 127, a timing belt 126 extended between the two pulleys 125, a linkage part X-axis guide rail 128, a guide member 128a which is engaged with the X-axis guide rail 128 so as to be guided, and an X-axis moving frame body 129 to which the guide member 128a is provided and which movably supports the linkage part 121 (that is, the detection part 120 and the board 123) in the Z-axis.

The X-axis moving frame body 129 is provided with the board 123, the linkage part 121, and the linkage part Z-axis moving mechanism for moving the detection part 120 in the vertical direction (the Z-axis direction). The linkage part Z-axis moving mechanism includes a Z-axis moving motor 122 attached to the X-axis moving frame body 129, a ball screw 122a driven by the motor 122, a nut part 124 into which the ball screw 122a is screwed, where the linkage part 121 (that is, the detection part 120) is attached to the nut part 124 (see FIGS. 6(a) and 6(b), and FIGS. 7(a) and 7(b)).

Note that the movement of the linkage part 121 (that is, the detection part 120) in the Y-axis direction (the row direction of the reaction vessels 116, 117) is carried out by the Y-axis moving mechanism for moving a nozzle head 108 in the Y-axis direction. The Y-axis moving mechanism 187y is provided with a guide rail extending in the Y-axis direction for guiding the nozzle head 108 by engaging with the lower end thereof. Note that the Y-axis moving mechanism has additionally mechanism elements such as a motor, pulleys and a timing belt (not shown).

The portion corresponding to reference sign 103 of the device 100 for measuring chemiluminescence is a connection end arrangement body including a plurality of (in this example, eight) connection ends 132 and an arrangement board 131, arranged on a horizontal straight line as the predetermined course, on which the connection ends 132 are arranged at predetermined intervals (for example, intervals between the adjacent reaction vessels 117).

Figure 8:
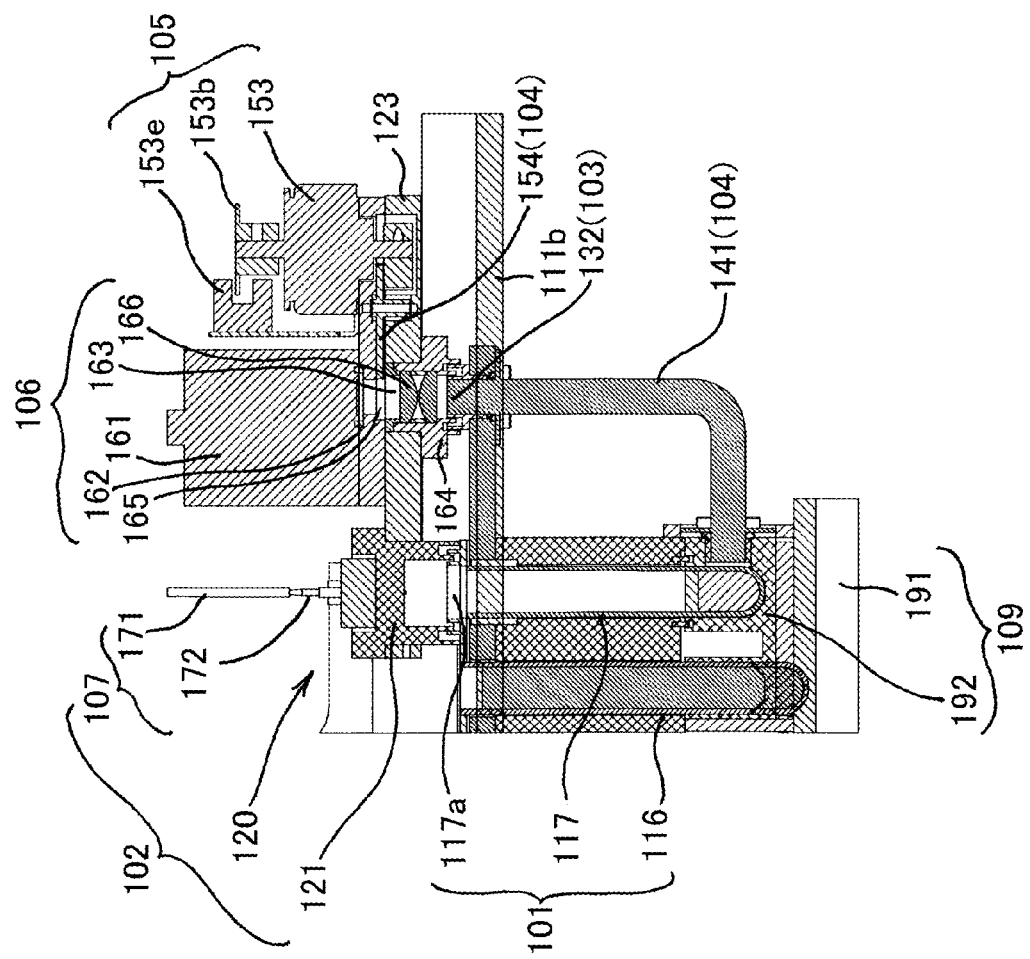
FIG. 8 is a cross sectional view taken along the CC line shown in FIGS. 7(a) and 7(b).
Figure 9:
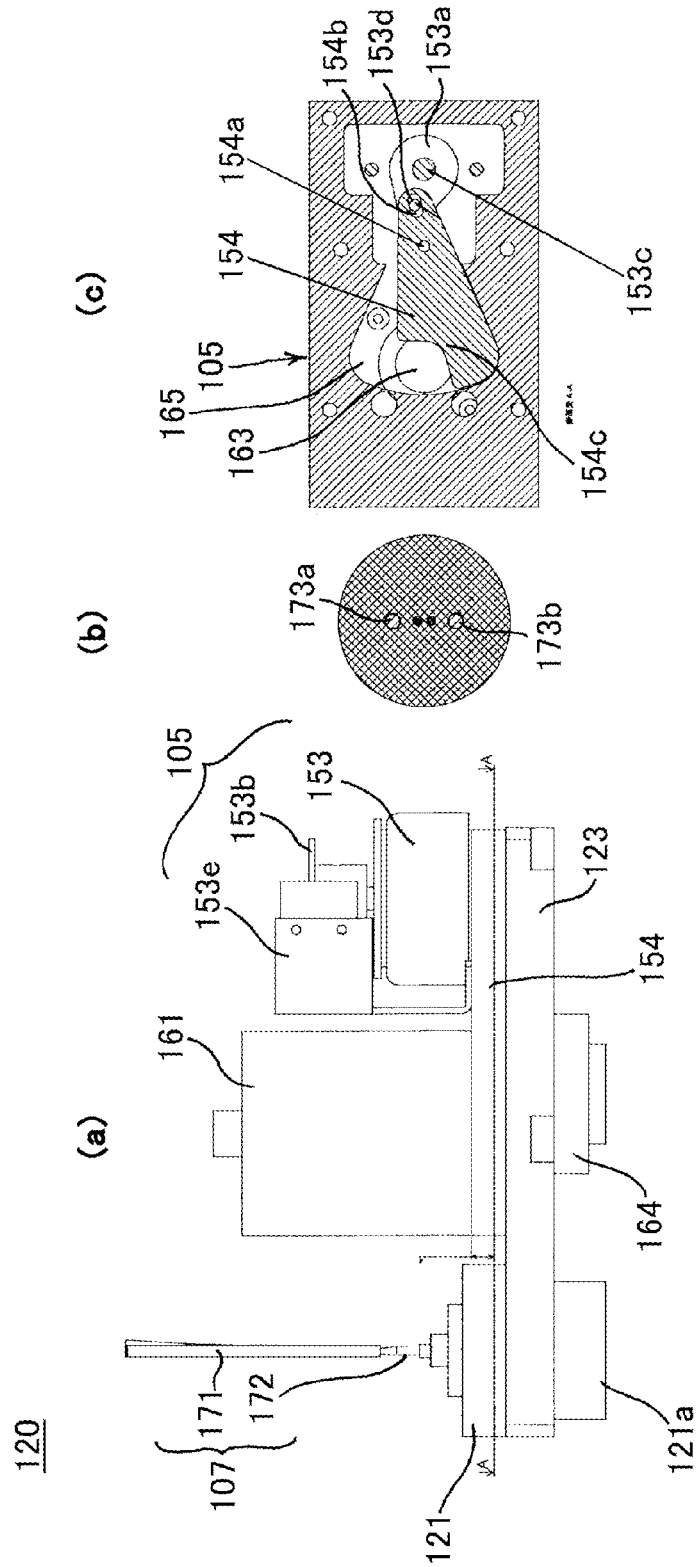
FIGS. 9(a) to 9(c) are detailed views showing the detection part shown in FIGS. 7(a) and 7(b).

As shown in FIG. 8, the light guiding parts 104 of the device 100 for measuring chemiluminescence include eight optical fibers 141, the front end of which is in proximity to the side of each of the translucent reaction vessels 117 for measurement and passes through each of the temperature control blocks 192 having alight shielding property, and the rear ends of which are provided to the plurality of (in this example, eight) connection ends 132. Note that reference sign 116 represents a reaction vessel for reagent reaction. Note that in the temperature control block 192, under which a fin 191 is provided, cooling is carried out by receiving wind from a blower 193.

Next, more detailed description of the detection part 120 is made based on FIG. 6(b), and FIGS. 7(a) and 7(b) to FIGS. 9(a) to 9(c). The detection part 120 has the linkage part 121, the shutter 105 and the photometer 106 provided to the board 123. The linkage part 121 has a fitting part 121a, the lower part of which is designed to fit into each of the openings 117a of the reaction vessel 117, and the upper part of which is provided with the reagent injection flow channel 171 capable of dispensing a trigger reagent when the front end thereof is located inside the reaction vessel 117 by means of the linkage of the linkage part 121 to the reaction vessel 117, which reagent injection flow channel 171 is formed of a flexible resin having a light shielding property. The fitting part 121a is provided with a packing having a light shielding property, or the like. In addition, the reaction vessels 117, the linkage part 121, the shutter 105 and the photometer 106 are individually formed of a light shielding member, coated with a light shielding membrane, or received in a dark room or a dark box.

As shown in FIG. 8, the photometer 106 of the device 100 for measuring chemiluminescence includes the PMT 161, a light reception tube 163, the lower end 164 of which is linked to the connection end 132 when the linkage part 121 is linked to the opening 117a of the reaction vessel 117, optical system combined lenses 166 provided within the light reception tube 163, a filter 162 through which only light in a predetermined wavelength range passes, and a gap part 165 for shielding guided light between the light reception tube 163 and the PMT 161 when the opening/closing plate 154 of the shutter 105 moves forward and bringing into a light guiding state therebetween when the opening/closing plate 154 moves backward.

As shown in FIGS. 9(a) to 9(c), the shutter 105 of the device 100 for measuring chemiluminescence includes a rotary solenoid 153 for rotating a rotary solenoid rotating shaft 153c from the reference position to a predetermined angle when the power supply is turned on and reversely rotating the rotating shaft 153c to return to the reference position by means of a spring when the power supply is turned off, a cam plate 153a attached to the rotary solenoid rotating shaft 153c, a shutter driving shaft 153d provided to the cam plate 153a, an opening/closing plate 154 which is driven following the movement of the cam plate 153a and has a cutout part 154c capable of optically connecting the light reception tube 163 to the PMT 161, the gap part 165 to which the opening/closing plate 154 and the cam plate 153a are movably provided and which is in communication with the light reception tube 163, a shutter rotating shaft 154a by which the opening/closing plate 154 is pivotally supported, a long hole 154b which is provided through the opening/closing plate 154 in the vicinity of one corner thereof and into which the shutter driving shaft 153d is loosely fitted, a rotary disc 153b which is attached to the rotary solenoid rotating shaft 153c and is provided outside the rotary solenoid 153, and an angle sensor 153e for detecting the angle of rotation of the rotary solenoid rotating shaft 153c based on the rotation of the rotary disc 153b.

In order to turn on the power supply of the rotary solenoid 153, the control part is provided with a photomicrosensor (LED, phototransistor) for emitting a beam of light which crosses a height position where the fitting part 121a of the detection part 120 covers the opening 117a of the reaction vessel 117, whereby a predetermined voltage is output when the beam of light is shut off by a light cut board provided to the detection part 120. Furthermore, in order to turn off the power supply of the rotary solenoid 153, the control part includes a timer for shutting off the output voltage after the linkage part 121 fits into the opening 117a of the reaction vessel 117, and then a predetermined measuring time (for example, a time until the chemiluminescence is completed, for example, several seconds) passes from injection of the trigger reagent.

As mainly shown in FIGS. 5, 7(a) and 7(b), the nozzle head 108 is provided with a plurality of (in this example, eight) cylinders 181 included in a suctioning and discharging mechanism 186 for carrying out suctioning and discharging of gas, a plurality of nozzles 182 which are in communication with the cylinders 181, and to the front ends of which, dispensing tips 184 for carrying out suctioning and discharging of liquid or the like are attachable, and a magnetic force means 185 capable of causing a magnetic field inside the dispensing tips 184 or the like. Here, reference sign 183 represents a frame body for supporting the nozzles and the like.

The dispensing tips or the like 184 are received in tip reception parts 115 mentioned below in a state where the plurality thereof (in this example, thirty-two) are attachable to the lower ends of the nozzles 182 (see FIGS. 12(a) to 12(c)). The suctioning and discharging mechanism 186 further includes, in addition to the cylinders 181, a detaching plate driving pin 186e for driving a detaching plate 186c for the dispensing tips or the like 184, to which a plurality of (in this example, eight) piston rods 186b of the cylinders 181 are attached, a motor 186a for moving upwardly and downwardly a plate 186d for suctioning and discharging, which allows descending a predetermined distance from a suctioning and discharging area of a liquid, engaging at the descended position and moving further in the downward direction, pulleys 186f, 186g, a timing belt 186h, a ball screw and the like. The upper portions of the nozzles 182 are provided with the detaching plate 186c through which a plurality of (in this example, eight) holes for detachment are provided, the inner diameter of which holes is larger than the outer diameter of the nozzles 182 but is smaller than the outer diameter of the dispensing tips or the like 184, so that each of the nozzles 182 passes therethrough. Accordingly, the driving in the downward direction by the plate 186d for suctioning and discharging allows the dispensing tips or the like 184 to be detached from the nozzles 182.

In addition, the nozzle head 108 includes, as a nozzle moving mechanism, a Z-axis moving mechanism 187z for moving the nozzles 182 in the Z-axis direction and a Y-axis moving mechanism 187y for moving the nozzles 182 in the Y-axis direction. Note that, in this example, the nozzles 182 do not move in the X-axis direction. The Z-axis moving mechanism 187z includes a motor 187a, pulleys 187b which are rotationally driven by the motor 187a, and a ball screw 187c which is rotationally driven by means of the rotation of the pulleys 187b (see FIGS. 7(a) and 7(b)), where the frame body 183 is attached to a nut part into which the ball screw 187c is screwed, so that the frame body 183 is moved upwardly and downwardly. Note that the Y-axis moving mechanism 187y for moving the nozzle head 187 with respect to the vessel group 101 in the Y-axis direction may be activated by including a guide rail 187e extending along the Y-axis direction for guiding the nozzle head 108 through engagement with the lower end thereof, and additionally providing the nozzle head 108 having a ball screw disposed along the Y-axis direction, a motor for rotationally driving the ball screw, and a nut part into which the ball screw is screwed. The Y-axis moving mechanism 187y provides the movement of the linkage part in the Y-axis direction.

The magnetic force means 185 has a plurality of (in this example, eight) permanent magnets 185a arranged on a magnet arrangement member in a line at the same intervals as those among the nozzles 182 along the X-axis direction. The magnet arrangement member is provided so as to come close to and separate from the dispensing tips or the like 184 attached to the nozzles 182 by the actuator 185b.

The temperature controller 109 of the device 100 for measuring chemiluminescence separately carries out collective temperature control of the plurality of (in this example, eight) reaction vessels 116 and the plurality of (in this example, eight) reaction vessels 117. The reaction vessels 116 are provided with a temperature control block 192, a fin 191 and a blower 193.

FIG. 10 to FIGS. 12(a) to 12(c) show in detail the first cartridge vessels 118 and the second cartridge vessels 119, each having eight, arranged to the vessel group 101 so as to extend along the Y-axis.

Figure 10:
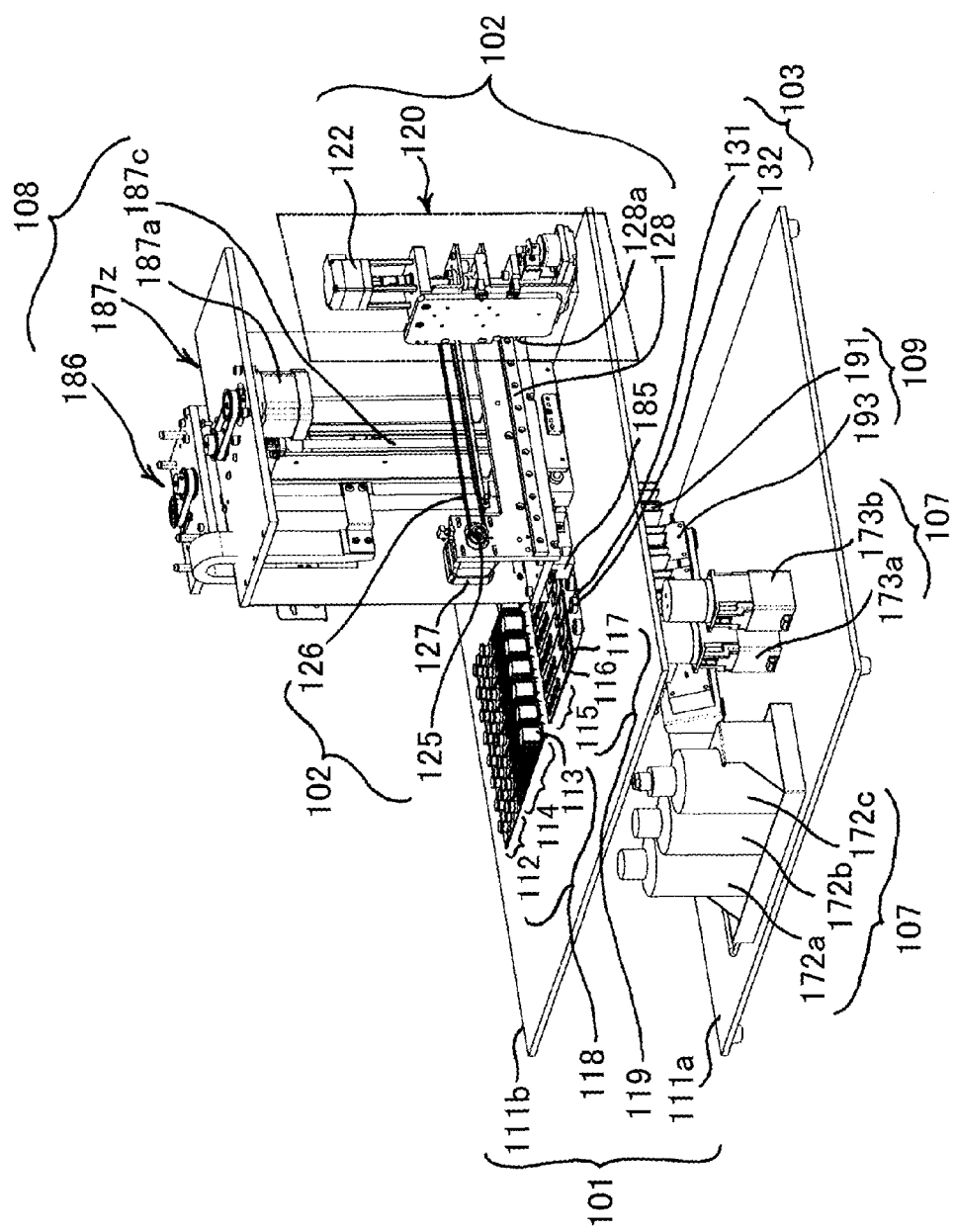
FIG. 10 is a partially omitted side perspective view showing the device of FIG. 5.
Figure 11:
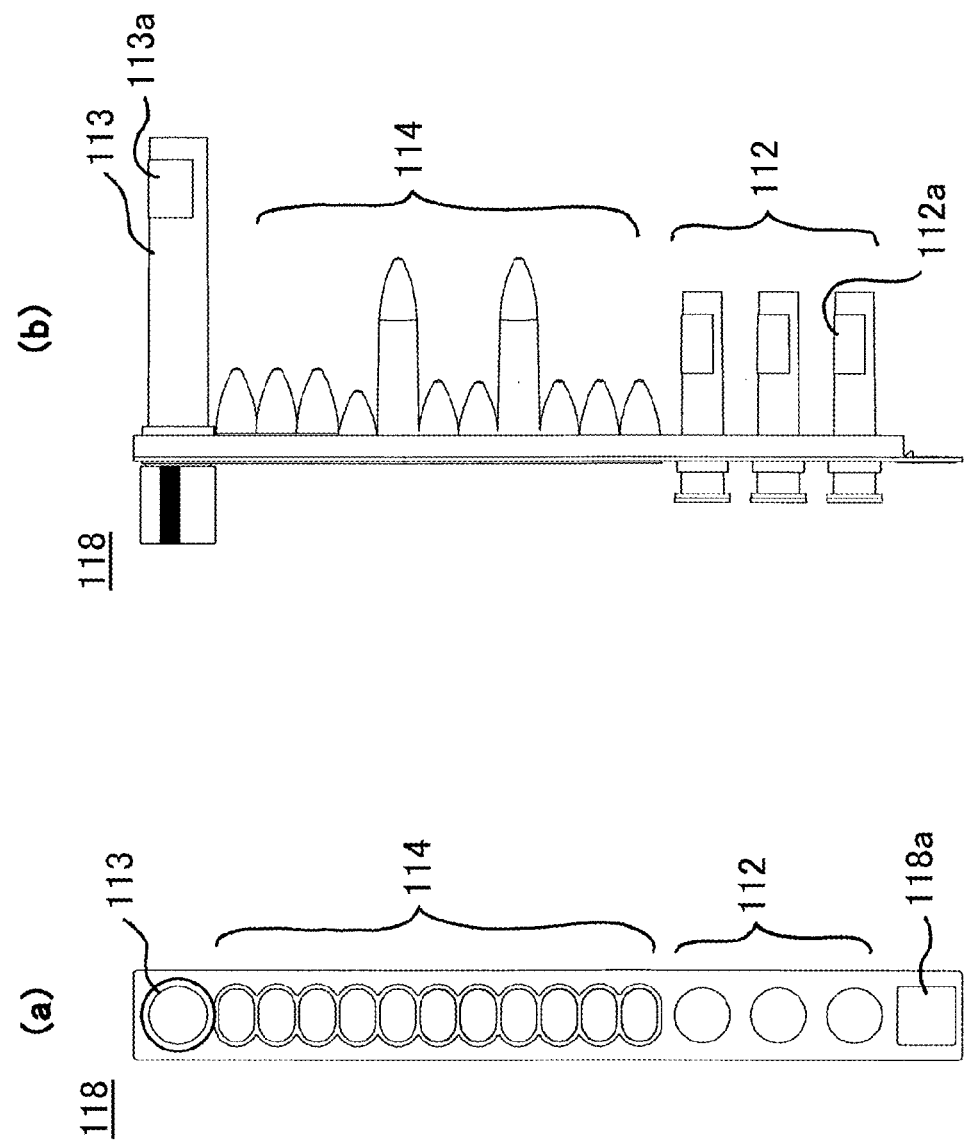
FIGS. 11(a) and 11(b) are an enlarged plan view and an enlarged side view of the first cartridge vessel shown in FIG. 10.
Figure 12:
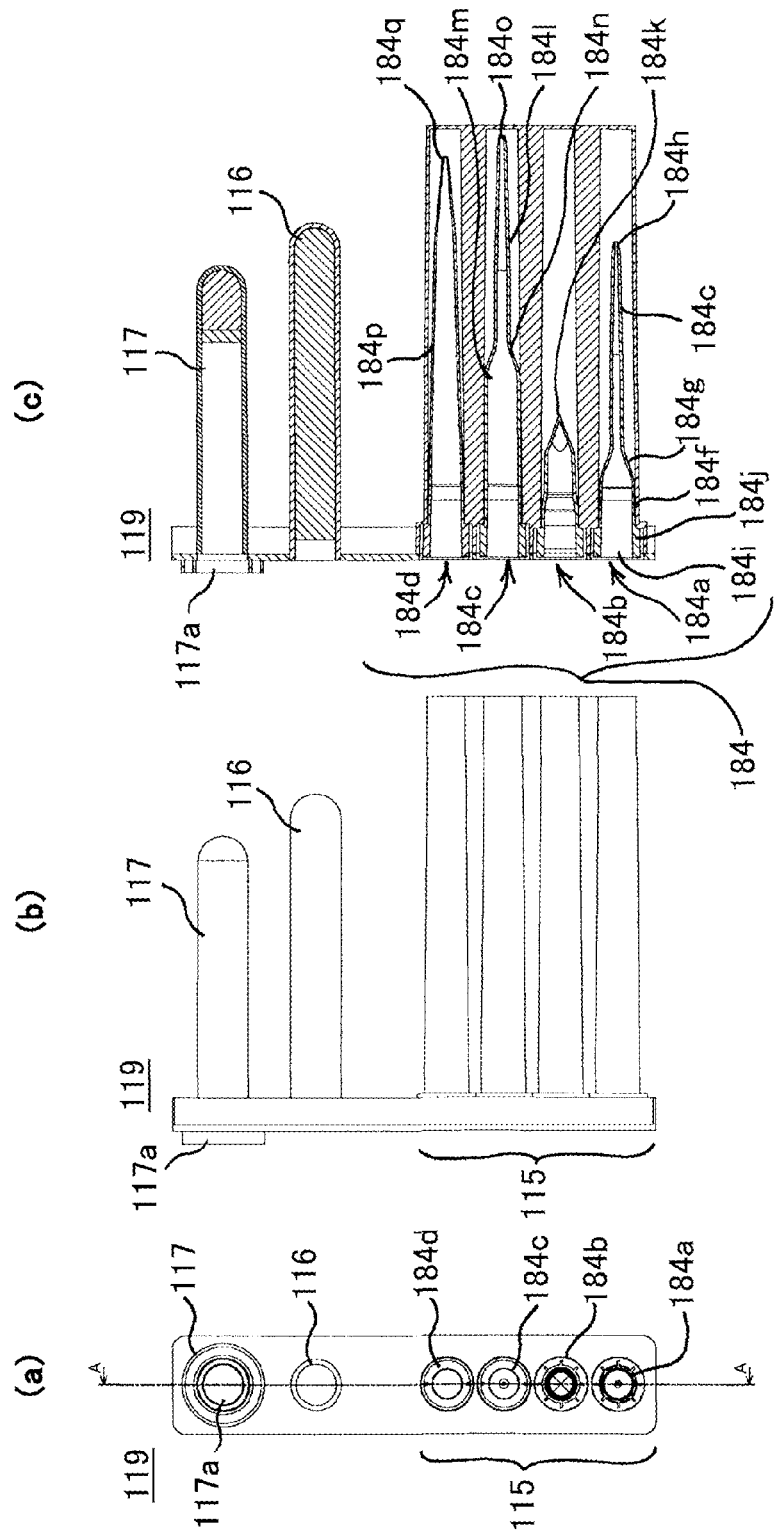
FIGS. 12(a) to 12(c) are an enlarged plan view, an enlarged side view and an enlarged cross sectional side view taken along the AA line of the second cartridge vessel shown in FIG. 10.

As shown in FIG. 10, a pair of the first cartridge vessel 118 and the second cartridge vessel 119 is arranged on the stage 111b of the device 100 for measuring chemiluminescence at a certain interval in a line along the Y-axis direction, and all of the eight pairs are arranged along the X-axis direction at regular intervals with the same pitch as that of the nozzles 182 provided to the nozzle head 108. The first cartridge vessel 118 and the second cartridge vessel 119 in each of the pairs are arranged on the movement course of each of the nozzles 182 of the nozzle head 108.

As shown in FIGS. 11(a) and 11(b), the first cartridge vessel 118 includes, as mentioned above, the sample reception part 113, the three reagent reception parts 112 for receiving a lyophilized reagent with covers consisting of a film which may be perforated, and the plurality of (in this example, eleven) reagent and solution reception parts 114 for receiving various reagents including a magnetic particle suspension containing magnetic particles for extracting a substance of interest to be targeted for measurement from the sample solution, a washing solution, a dissociating solution, as a substance for chemiluminescence, for example, an acridinium-labeled antibody, a trigger reagent (e.g., $H_2O_2$) and an NaOH solution, and the like. The liquid reception parts 114 are provided with liquid reception parts having various kinds of volumes. Note that reference sign 118a represents a label on which cord data is expressed indicating sample information and/or examination information about the first cartridge vessel 118, and reference signs 112a, 113a also represent labels on which information corresponding to each of the reception parts is indicated by cord data or handwriting.

As shown in FIGS. 12(a) to 12(c), the second cartridge vessels 119 include, as mentioned above, in addition to the reaction vessels 116, 117 to which temperature control is carried out by the temperature control block 192, the tip reception parts 115 for receiving the plurality of (in this example, thirty-two) dispensing tips 184a or the like in an attachable state by means of the descent of the nozzles 182. The reaction vessel 116 is a vessel for carrying out mixing of a reagent, a solution or the like and promoting the reaction of a sample with the reagent, whereas the reaction vessel 117 is a vessel for measuring the amount of luminescence from chemiluminescence by means of injection of the trigger reagent.

In the tip reception parts 115 are received various tips 184 commonly having openings 184i for attachment which are detachably attachable to the nozzles 182 and projected rims provided on the lateral surface of the openings for attachment, examples thereof including small volume dispensing tips 184a, tips 184b for perforation, large volume dispensing tips 184c and tips 184d for sample.

The small volume (large volume) dispensing tip 184a (184c) includes a narrow tube 184e (184l) which is formed to be tapered so as to have a mouth part 184h (184o) at the front end, and a thick tube 184f (184m) which is formed to be thicker than the narrow tube 184e (184l), has the opening 184i for attachment and is in communication with the narrow tube 184e (184l) through a transition part 184g (184n). The outside of the thick tube 184f (184m) is provided with a projected rim 184j. The tip 184b for perforation has a tapered tip end 184k. The tip 184d for sample includes a tube 184p which has a mouth portion 184q at the front end and is formed to be tapered from the opening 184i for attachment provided at the rear end toward the mouth portion 184q at the front end, by which a sample may be stored thereinside. Note that it is possible in the small volume dispensing tip 184a and the large volume dispensing tip 184d to cause a magnetic field inside the narrow tube 184e, 184l by causing a magnet 185a to come close to the narrow tube 184e, 184l.

Next, a description is made of the motion of the device 100 for measuring chemiluminescence according to the embodiments.

A description is made of a case of preparing a tracer in immunoassay by directly labeling an antigen substance or an antibody substance as the substance of interest in serum with the use of an acridinium ester derivative as a compound for chemiluminescence method.

In step S101, a serum sample solution collected from each of eight patients is received in each of the sample reception parts 113.

In step S102, moving the nozzles 182 of the nozzle head 108 by the Y-axis moving mechanism 187y above the tips 184b for perforation in the tip reception parts 115 and causing the nozzles 182 to descend along the Z-axis direction allow the eight tips 184b for perforation to be attached to the nozzles 182. By moving the tips 184b for perforation upwardly and sequentially moving the tips 184b with respect to each of the reception parts 112, 114, 113 in the first cartridge vessels 118, the film covering the opening of each of the reception parts is perforated by the tip end 184k.

In step S103, moving the nozzle head 108 in the Y-axis direction, moving the tips 184b for perforation above the original reception part of the tip reception parts 115, and causing the piston rods 186b to descend beyond a certain distance by the motor 186a for suctioning and discharging provided to the nozzle head 108 allow the detaching plate driving pin 186e to be pressed down and thus the detaching plate 186c to be pressed down so that the tips 184b for perforation are detached from the nozzles 182 into the original reception parts.

In step S104, moving the nozzles 182 of the nozzle head 108 by the Y-axis moving mechanism 187y above the tips 184d for sample in the tip reception parts 115 and causing the nozzles 182 to descend along the Z-axis direction allow the eight tips 184d for sample to be attached to the nozzles 182. After moving the tips 184d for sample upwardly and moving the tips 184d for sample above the sample reception parts 113 by the Y-axis moving mechanism 187y, 0.1 mL from the sample reception parts 113 for example, of the serum sample vessels are suctioned and discharged into the reaction vessels 116 all at once.

In step S105, moving the nozzle head 108 in the Y-axis direction, moving the tips 184d for sample contaminated with the sample above the original reception parts of the tip reception parts 115, and causing the piston rods 186b to descend beyond a certain distance by the motor 186a for suctioning and discharging provided to the nozzle head 108 allow the detaching plate driving pin 186e to be pressed down and the detaching plate 186c to be pressed down so that the tips 184d for sample are detached from the nozzles 182 into the original reception parts.

Next, in step S106, the new dispensing tips 184a which are received at the smaller position in the Y coordinate of the tip reception parts 115 are attached to the nozzles 182. Then, the nozzle head 108 is moved in the Y-axis direction to suction 0.1 mL of an acridinium-labeled antibody received in any of the liquid reception parts 114, and is moved in the Y-axis direction to the eight reaction vessels 116 to discharge the same, followed by incubation at room temperature for 120 minutes.

In step S107, moving the nozzle head 108 along the Y-axis, in order to examine the antigen substance in the serum targeted for measurement, transferring the dispensing tips 184a attached to the nozzle 182 above any of the reagent reception parts 114 in which the magnetic particle suspension is received in which the magnetic particles, onto the surface of which the antibody capable of specifically binding to the antigen substance is fixed, are suspended, causing the dispensing tips 184a to descend with the use of the Z-axis moving mechanism 187z, inserting the front ends of the dispensing tips 184a inside the reagent reception parts 114, suctioning 0.5 mL of the received magnetic particle suspension into the dispensing tips 184a, causing the dispensing tips 84 to ascend with the use of the Z-axis moving mechanism 187z, moving the dispensing tips 84 in the reaction vessels 116 by the Y-axis moving mechanism 187y, causing the dispensing tips 84 to descend with the use of the Z-axis moving mechanism 187z, discharging the suspension into the reaction vessels 116 while moving the piston rods 186b upwardly and downwardly, and repeating the suctioning and discharging result in stirring.

In step S108, in a state of bringing the dispensing tips 184a to a standstill at a predetermined height position by the Z-axis moving mechanism 187z and causing the magnets 185a to come close to each of the dispensing tips 184a all at once with the use of the magnetic force means 85, repeating the suctioning and discharging by moving the plate for suctioning and discharging upwardly and downwardly, moving the nozzle head 108 by the Y-axis moving mechanism 187y with the magnets 185a being close to the dispensing tips 184a so as to be located above the reagent reception parts 114 in which the washing solution is received, causing the dispensing tips 184a to descend by the Z-axis moving mechanism 187z, and, in a state where the magnets 185a are separated, repeating the suctioning and discharging allow washing, so that B/F separation is carried out.

In step S109, in a state where the magnetic particles are attracted to the inner wall again by causing the magnets 185a of the magnetic force means 185 to come close to the dispensing tips 184a, moving the dispensing tips 184a by the Y-axis moving mechanism 187y to the reaction vessels 117 in which, for example, 0.1 mL of water is received, inserting the dispensing tips 184 into the reaction vessels 117 by the Z-axis moving mechanism 187z, re-suspending the magnetic particles in the liquid in a state where the magnets 185a are separated allow the labeled substance of interest to be dissociated from the magnetic particles, followed by removal of the magnetic particles.

In step S110, driving the X-axis moving motor 127 of the linkage part moving mechanism causes the linkage part 121 to move along the X-axis so as to locate above the first reaction vessel 117, and then causing the linkage part 121 to descend by the Z-axis moving motor 122 of the Z-axis moving mechanism or the like allow the fitting part thereof to fit into the opening 117a of the reaction vessel 117, thereby forming a confined space shielded from external light in combination with the reaction vessel 117. In doing so, the lower end 164 of the light reception tube 163 will connect to the connection end 132. In the state where the lower end 164 of the light reception tube 163 connects to the connection end 132, the control part turns on an electrical signal for driving the shutter 105 interlocking with the linkage, and rotates the cam plate 153a at a predetermined angle by the rotary solenoid 153 of the shutter 105, so that the shutter driving shaft 153d provided to the cam plate 153a slides in the long hole 154b so as to rotate the opening/closing plate 154, thereby optically connecting the light reception tube 163 to the connection end 132. Accordingly, the linkage of the linkage part 121 through the opening 117a of the reaction vessel 117 brings into a light guiding state from the reaction vessel 117 to the PMT 161. Note that, when the linkage part 121 moves to the second reaction vessel 117, the control part turns off the electrical signal so as to reversely rotate the rotary solenoid 153 to the original state by means of the spring power, thereby moving the opening/closing plate 154, so that a light shielding state will be brought between the light reception tube 163 and the connection end 132.

In step S111, through the reagent injection flow channel 171, which is provided to the linkage part 121, and the front end of which is located inside the reaction vessel 117 by means of the linkage to the reaction vessel 117, 0.2 mL of H2O2, which is a trigger reagent as a reagent for chemiluminescence, and 0.2 mL of 0.2 N NaOH are injected into the reaction vessel 117, so that chemiluminescence is produced, and light receiving will be carried out by the PMT 161 for a predetermined measuring time. After the predetermined measuring time passes, rotating the opening/closing plate 154 in the reverse direction by the spring power, thereby bringing into a light shielding state between the light reception tube 163 and the connection end 132. Thereafter, causing the linkage part 121 to ascend in the Z-axis direction, thereby releasing the linkage of the opening 117a of the first reaction vessel 117 to the fitting part, while releasing the connection of the lower end 164 of the light reception tube 163 to the connection end 132, so that the linkage part 121 separates from the first reaction vessel 117 and moves to the second reaction vessel, in which the same treatment as for the first reaction vessel 117 will be carried out. In this way, the treatments are sequentially carried out for the eight reaction vessels 117. According to these embodiments, because the light reception switching mechanism may serve as the linking mechanism, it is possible to reduce the number of parts.

The specific description of each of the above mentioned embodiments is made only to lead to a better understanding of the present invention, but does not limit other embodiments. Accordingly, it is possible to carry out modification without departing from the spirit of the present invention. Also, the reagent for chemiluminescence is not limited to an acridinium ester derivative nor limited to the above mentioned reagents.

In addition, a description is made of only the embodiment for CLIA assay, but the present invention may also be applied to a CLEIA assay which does not use the reagent injection flow channel.

In addition, a description is made of only the case of using one PMT, but it is possible to carry out measurement using a plurality of PMTs without using, for example, the connection end arrangement body.

Furthermore, a description is made of only the case of using one linkage part, but it is also possible to use a plurality of the linkage parts in the same way.

A description is made of only the case of combination with the nozzle head, but it is also possible to carry out measurement without using the nozzle head.

In addition, the numerical value, the number of times, the shape, the number of parts, the amount or the like used in the above mentioned description is not limited to this case. For example, a description is made of the case where eight each of the cartridge vessels, reaction vessels, nozzles and connection ends are provided, but it goes without saying that the present invention is not limited to the number of parts.

Furthermore, the above mentioned individual components, for example, the vessel group, the linking mechanism, the connection end arrangement body, the light reception switching mechanism, the light guiding part, the shutter, the photometer, the reagent injecting mechanism, the nozzle head, the temperature controller, the device for measuring chemiluminescence or the like, a device formed from these components, parts or components composing these components or the like may be freely combined with an appropriate modification.

INDUSTRIAL APPLICABILITY

The present invention relates to a device and method for measuring chemiluminescence, which carry out examination of samples collected from patients or the like, optical measurement thereof and analysis thereof, and which are available in fields, in particular, in which handling of biomacromolecule or low biomolecule such as gene, immune system, amino acid, protein or sugar is required, for example, various fields such as a biochemical field, an industrial field, an agricultural field including food, agricultural production, seafood processing or the like, a pharmaceutical field, and a medical care field including hygiene, health, immunity, disease, heredity or the like.

REFERENCE SIGNS LIST 1, 101 vessel group
2, 102 linking mechanism
3 (103) connection end arrangement body and light reception switching mechanism (connection end arrangement body)
4, 104 light guiding part
5, 105 shutter
6, 106 photometer
7, 107 reagent injecting mechanism
8, 108 nozzle head
9, 109 temperature controller
10, 100 device for measuring chemiluminescence

The invention claimed is:

1. A device for measuring chemiluminescence, comprising:
   a reaction vessel;
   a dispensing tip configured to receive a sample containing a substance of interest, a chemiluminescence labeling substance that labels the substance of interest, and magnetic particles to which the substance of interest in the sample is bound;
   a magnet configured to apply a magnetic field to the dispensing tip to separate the magnetic particles from the rest of the sample;
   a suction and discharge mechanism in communication with the dispensing tip and configured to:
      dissociate the labeled substance of interest from the separated magnetic particles, and
      dispense the dissociated labeled substance of interest from the dispensing tip into the reaction vessel;
   a linkage part configured to be linked to an opening of the reaction vessel to form a confined space inside the linked reaction vessel that is shielded from external light;
   a reagent injection flow channel coupled to the linkage part and configured to inject a reagent for producing chemiluminescence into the linked reaction vessel;
   a photometer configured to measure an optical state in the linked reaction vessel for a predetermined measuring time after the reagent injection flow channel injects the reagent for producing chemiluminescence into the linked reaction vessel; and
   a shutter configured to:
      establish a light guiding state between the photometer and the confined space inside the linked reaction vessel, and
      switch from the light guiding state to a light shielding state between the photometer and the confined space inside the linked reaction vessel after the predetermined measuring time passes and before release of the linkage part from the linked reaction vessel.

2. The device for measuring chemiluminescence according to claim 1, further comprising:
   a light guiding part configured to guide light between the reaction vessel and the photometer when the shutter is in the light guiding state.

3. The device for measuring chemiluminescence according to claim 2, further comprising:
   one or more additional reaction vessels to which the linkage part is configured to be linked;
   one or more additional light guiding parts configured to guide light between the respective additional reaction vessels and the photometer when the shutter is in the light guiding state;
   an arrangement body to which respective first ends of the light guiding part and the additional light guiding parts are coupled along a predetermined course; and
   a light reception switching mechanism configured to sequentially optically connect the respective first ends of the light guiding part and the additional light guiding parts to the photometer by moving one or both of the arrangement body and the photometer along the predetermined course,
   wherein respective second ends of the light guiding part and the additional light guiding parts are in proximity to, or in contact with, the reaction vessel and the additional reaction vessels, respectively.

4. The device for measuring chemiluminescence according to claim 3, wherein the light reception switching mechanism optically connects the photometer to the first end of the light guiding part whose second end is in proximity to, or in contact with, the linked reaction vessel.

5. The device for measuring chemiluminescence according to claim 3, further comprising:
   a reagent injecting mechanism coupled to the reagent injection flow channel to inject the reagent for producing chemiluminescence through the reagent injection flow channel and into the linked reaction vessel;
   wherein before, or during, the injection of the reagent for producing chemiluminescence into the linked reaction vessel, the shutter is configured to establish the light guiding state between the photometer and the confined space inside the linked reaction vessel.

6. The device for measuring chemiluminescence according to claim 2, further comprising:
   a reagent injecting mechanism coupled to the reagent injection flow channel to inject the reagent for producing chemiluminescence through the reagent injection flow channel and into the linked reaction vessel;
   wherein before, or during, the injection of the reagent for producing chemiluminescence into the linked reaction vessel, the shutter is configured to establish the light guiding state between the photometer and the confined space inside the linked reaction vessel.

7. The device for measuring chemiluminescence according to claim 1, further comprising:
a reagent injecting mechanism coupled to the reagent injection flow channel to inject the reagent for producing chemiluminescence through the reagent injection flow channel and into the linked reaction vessel;
wherein before, or during, the injection of the reagent for producing chemiluminescence into the linked reaction vessel, the shutter is configured to establish the light guiding state between the photometer and the confined space inside the linked reaction vessel.

8. A method for measuring chemiluminescence, the method comprising:
receiving, into a dispensing tip, a sample containing a substance of interest, a chemiluminescence labeling substance to label the substance of interest, and magnetic particles to which the substance of interest in the sample is bindable;
labeling the substance of interest with the chemiluminescence labeling substance;
applying a magnetic field to the dispensing tip to separate the magnetic particles from the rest of the sample;
dissociating the labeled substance of interest from the separated magnetic particles;
dispensing the dissociated labeled substance of interest into a reaction vessel;
linking a linkage part to an opening in the reaction vessel to form a confined space inside the linked reaction vessel that is shielded from external light;
injecting a reagent for producing chemiluminescence into the linked reaction vessel from a reagent injection flow channel coupled to the linkage part;
establishing, using a shutter, a light guiding state between a photometer and the confined space inside the linked reaction vessel;
measuring an optical state in the linked reaction vessel, using the photometer, for a predetermined measuring time after injection of the reagent for producing chemiluminescence into the linked reaction vessel; and
switching the shutter from the light guiding state to a light shielding state between the photometer and the confined space inside the linked reaction vessel after the predetermined measuring time passes and before release of the linkage part from the linked reaction vessel.

9. The method for measuring chemiluminescence according to claim 8,
wherein the predetermined measuring time depends on one or more factors selected from the group consisting of:
sensitivity of the photometer,
kind of the reagent for producing chemiluminescence,
amount of the reagent for producing chemiluminescence, and
lifetime of the chemiluminescence.

10. The method for measuring chemiluminescence according to claim 9, further comprising:
sequentially optically connecting, using a light reception switching mechanism, respective first ends of one or more light guiding parts to the photometer, the respective first ends of the light guiding parts being coupled to an arrangement body along a predetermined course, and the light guiding parts having respective second ends in proximity to, or in contact with, the reaction vessel and one or more additional reaction vessels to which the linkage part is configured to be linked;
wherein the light reception switching mechanism moves one or both of the arrangement body and the photometer along the predetermined course to sequentially optically connect the respective first ends of the light guiding parts to the photometer.

11. The method for measuring chemiluminescence according to claim 8, further comprising:
sequentially optically connecting, using a light reception switching mechanism, respective first ends of one or more light guiding parts to the photometer, the respective first ends of the light guiding parts being coupled to an arrangement body along a predetermined course, and the light guiding parts having respective second ends in proximity to, or in contact with, the reaction vessel and one or more additional reaction vessels to which the linkage part is configured to be linked;
wherein the light reception switching mechanism moves one or both of the arrangement body and the photometer along the predetermined course to sequentially optically connect the respective first ends of the light guiding parts to the photometer.

12. A device for measuring chemiluminescence, comprising:
a reaction vessel;
a linkage part configured to be linked to an opening of the reaction vessel to form a confined space inside the linked reaction vessel that is shielded from external light;
a reagent injection flow channel coupled to the linkage part and configured to inject a reagent for producing chemiluminescence into the linked reaction vessel;
a photometer configured to measure an optical state in the linked reaction vessel for a predetermined measuring time after the reagent injection flow channel injects the reagent for producing chemiluminescence into the linked reaction vessel; and
a shutter configured to:
establish a light guiding state between the photometer and the confined space inside the linked reaction vessel, and
switch from the light guiding state to a light shielding state between the photometer and the confined space inside the linked reaction vessel after the predetermined measuring time passes.

13. The device for measuring chemiluminescence according to claim 12, further comprising:
a light guiding part configured to guide light between the reaction vessel and the photometer when the shutter is in the light guiding state.

14. The device for measuring chemiluminescence according to claim 13, further comprising:
one or more additional reaction vessels to which the linkage part is configured to be linked;
one or more additional light guiding parts configured to guide light between the respective additional reaction vessels and the photometer when the shutter is in the light guiding state;
an arrangement body to which respective first ends of the light guiding part and the additional light guiding parts are coupled along a predetermined course; and
a light reception switching mechanism configured to sequentially optically connect the respective first ends of the light guiding part and the additional light guiding parts to the photometer by moving one or both of the arrangement body and the photometer along the predetermined course, wherein respective second ends of the light guiding part and the additional light guiding parts are in proximity to, or in contact with, the reaction vessel and the additional reaction vessels, respectively.

15. The device for measuring chemiluminescence according to claim 14, wherein the light reception switching mechanism optically connects the photometer to the first end of the light guiding part whose second end is in proximity to, or in contact with, the linked reaction vessel.

16. The device for measuring chemiluminescence according to claim 12, further comprising:
a reagent injecting mechanism coupled to the reagent injection flow channel to inject the reagent for producing chemiluminescence through the reagent injection flow channel and into the linked reaction vessel;
wherein before, or during, the injection of the reagent for producing chemiluminescence into the linked reaction vessel, the shutter is configured to establish the light guiding state between the photometer and the confined space inside the linked reaction vessel.

17. A method for measuring chemiluminescence, the method comprising:
labeling a substance of interest with a chemiluminescence labeling substance;
dispensing the labeled substance of interest into a reaction vessel;
linking a linkage part to an opening in the reaction vessel to form a confined space inside the linked reaction vessel that is shielded from external light;
injecting a reagent for producing chemiluminescence into the linked reaction vessel from a reagent injection flow channel coupled to the linkage part;
establishing, using a shutter, a light guiding state between a photometer and the confined space inside the linked reaction vessel;
measuring an optical state in the linked reaction vessel, using the photometer, for a predetermined measuring time after injection of the reagent for producing chemiluminescence into the linked reaction vessel; and
switching the shutter from the light guiding state to a light shielding state between the photometer and the confined space inside the linked reaction vessel after the predetermined measuring time passes.

18. The method for measuring chemiluminescence according to claim 17, wherein the predetermined measuring time depends on one or more factors selected from the group consisting of:
sensitivity of the photometer,
kind of the reagent for producing chemiluminescence,
amount of the reagent for producing chemiluminescence, and
lifetime of the chemiluminescence.

19. The method for measuring chemiluminescence according to claim 17, further comprising:
sequentially optically connecting, using a light reception switching mechanism, respective first ends of one or more light guiding parts to the photometer, the respective first ends of the light guiding parts being coupled to an arrangement body along a predetermined course, and the light guiding parts having respective second ends in proximity to, or in contact with, the reaction vessel and one or more additional reaction vessels to which the linkage part is configured to be linked;
wherein the light reception switching mechanism moves one or both of the arrangement body and the photometer along the predetermined course to sequentially optically connect the respective first ends of the light guiding parts to the photometer.

\* \* \* \* \*